US012704576B2

(12) United States Patent
Zhou et al.

(10) Patent No.: US 12,704,576 B2
(45) Date of Patent: Aug. 11, 2026

(54) EPI DATA CORRECTION METHOD AND DEVICE AND MRI SYSTEM

(71) Applicant: Siemens Healthineers AG, Forchheim (DE)

(72) Inventors: Kun Zhou, Shenzhen (CN); Wei Liu, Erlangen (DE); Yulin Chang, Belmont, MA (US)

(73) Assignee: Siemens Healthineers AG, Forchheim (DE)

( * ) Notice: Subject to any disclaimer, the term of this patent is extended or adjusted under 35 U.S.C. 154(b) by 323 days.

(21) Appl. No.: 18/615,230

(22) Filed: Mar. 25, 2024

(65) Prior Publication Data

US 2024/0329173 A1 Oct. 3, 2024

(30) Foreign Application Priority Data

Mar. 27, 2023 (CN) ......................... 202310330106.7

(51) Int. Cl.
*G01R 33/561* (2006.01)
*A61B 5/055* (2006.01)

(52) U.S. Cl.
CPC .......... *G01R 33/5616* (2013.01); *A61B 5/055* (2013.01)

(58) Field of Classification Search
CPC ............................ A61B 5/055; G01R 33/5616
See application file for complete search history.

(56) References Cited

U.S. PATENT DOCUMENTS 10,175,328 B2 * 1/2019 Hoge ................... G01R 33/561
11,009,577 B2 * 5/2021 McKay .............. G01R 33/5611
11,169,236 B2 * 11/2021 Zhou ................ G01R 33/56545

OTHER PUBLICATIONS

Yulin V Chang et al. "Inter-Frame Phase Alignment for Echo Planar Imaging Calibration Data Acquired with Opposite Read-Out Polarities" Proc. Intl. Soc. Mag. Reson. Med. 27 (2019); 2019.

Polimeni, Jonathan R. et al. "Reducing Sensitivity Losses Due to Respiration and Motion in Accelerated Echo Planar Imaging By Reordering The Autocalibration Data Acquisition" Magnetic Resonance in Medicine; vol. 75; pp. 665-679; 2016.

Hoge W. Scott, et al. "Dual-Polarity GRAPPA for Simultaneous Reconstruction and Ghost Correction of Echo Planar Imaging Data" Magnetic Resonance in Medicine, 2016, 76:32-44, 32 pages; 2016.

* cited by examiner

*Primary Examiner* — Gregory H Curran
(74) *Attorney, Agent, or Firm* — Banner & Witcoff, Ltd.

(57) ABSTRACT

Echo planar imaging scanning techniques are provided. In a single excited EPI scanning process, a 90° RF excited pulse is applied to a target tissue. Then, a first RF convergence pulse is applied, followed by a first readout gradient pulse sequence in a readout direction while forbidding phase encoding gradients in a phase encoding direction and simultaneously collecting data for correcting a phase error between k-space lines. After the first readout gradient pulse sequence is applied, the first RF convergence pulse is sequentially applied to the target tissue for R times at intervals, and after the first RF convergence pulse is applied each time, the first readout gradient pulse sequence is applied in the readout direction while simultaneously applying a first phase encoding pulse sequence in the phase encoding direction, and collecting ACS data in a segmented manner, where R is an in-layer phase direction acceleration factor.

18 Claims, 10 Drawing Sheets

100

Applying a 90° RF excited pulse to a target tissue, and simultaneously applying a first layer selection gradient pulse to the target tissue in a layer selection encoding direction
101

Applying a first RF convergence pulse to the target tissue, and simultaneously applying a second layer selection gradient pulse to the target tissue in the layer selection encoding direction
102

Applying a first readout gradient pulse sequence to the target tissue in a readout direction, forbidding phase encoding gradients in a phase encoding direction, and simultaneously turning on an ADC to collect data for correcting a phase error between K-space lines
103

Turning off the ADC;
sequentially applying the first RF convergence pulse to the target tissue for R times at intervals;
applying the second layer selection gradient pulse to the target tissue in the layer selection encoding direction while the first radio-frequency convergence pulse is applied each time;
after the first RF convergence pulse is applied each time, applying the first readout gradient pulse sequence to the target tissue in the readout direction, simultaneously applying a first phase encoding pulse sequence in the phase encoding direction;
simultaneously turning on the ADC to collect auto calibration signal (ACS) data in a segmented manner; applying a phase encoding pulse to the target tissue in the phase encoding direction
104

Figure 1:
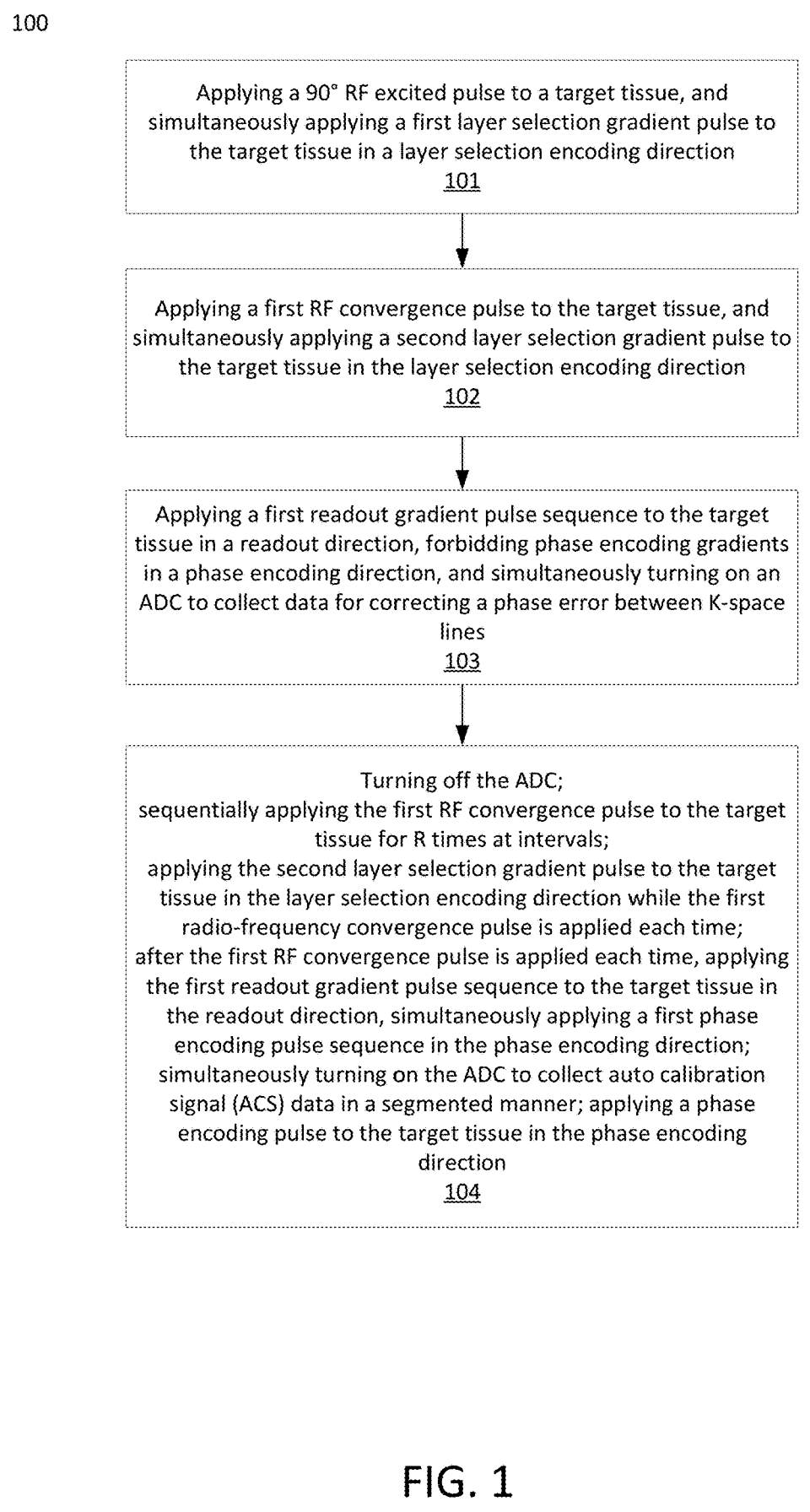

100

Applying a 90° RF excited pulse to a target tissue, and simultaneously applying a first layer selection gradient pulse to the target tissue in a layer selection encoding direction
101

Applying a first RF convergence pulse to the target tissue, and simultaneously applying a second layer selection gradient pulse to the target tissue in the layer selection encoding direction
102

Applying a first readout gradient pulse sequence to the target tissue in a readout direction, forbidding phase encoding gradients in a phase encoding direction, and simultaneously turning on an ADC to collect data for correcting a phase error between K-space lines
103

Turning off the ADC;
sequentially applying the first RF convergence pulse to the target tissue for R times at intervals;
applying the second layer selection gradient pulse to the target tissue in the layer selection encoding direction while the first radio-frequency convergence pulse is applied each time;
after the first RF convergence pulse is applied each time, applying the first readout gradient pulse sequence to the target tissue in the readout direction, simultaneously applying a first phase encoding pulse sequence in the phase encoding direction;
simultaneously turning on the ADC to collect auto calibration signal (ACS) data in a segmented manner; applying a phase encoding pulse to the target tissue in the phase encoding direction
104

Figure 5:
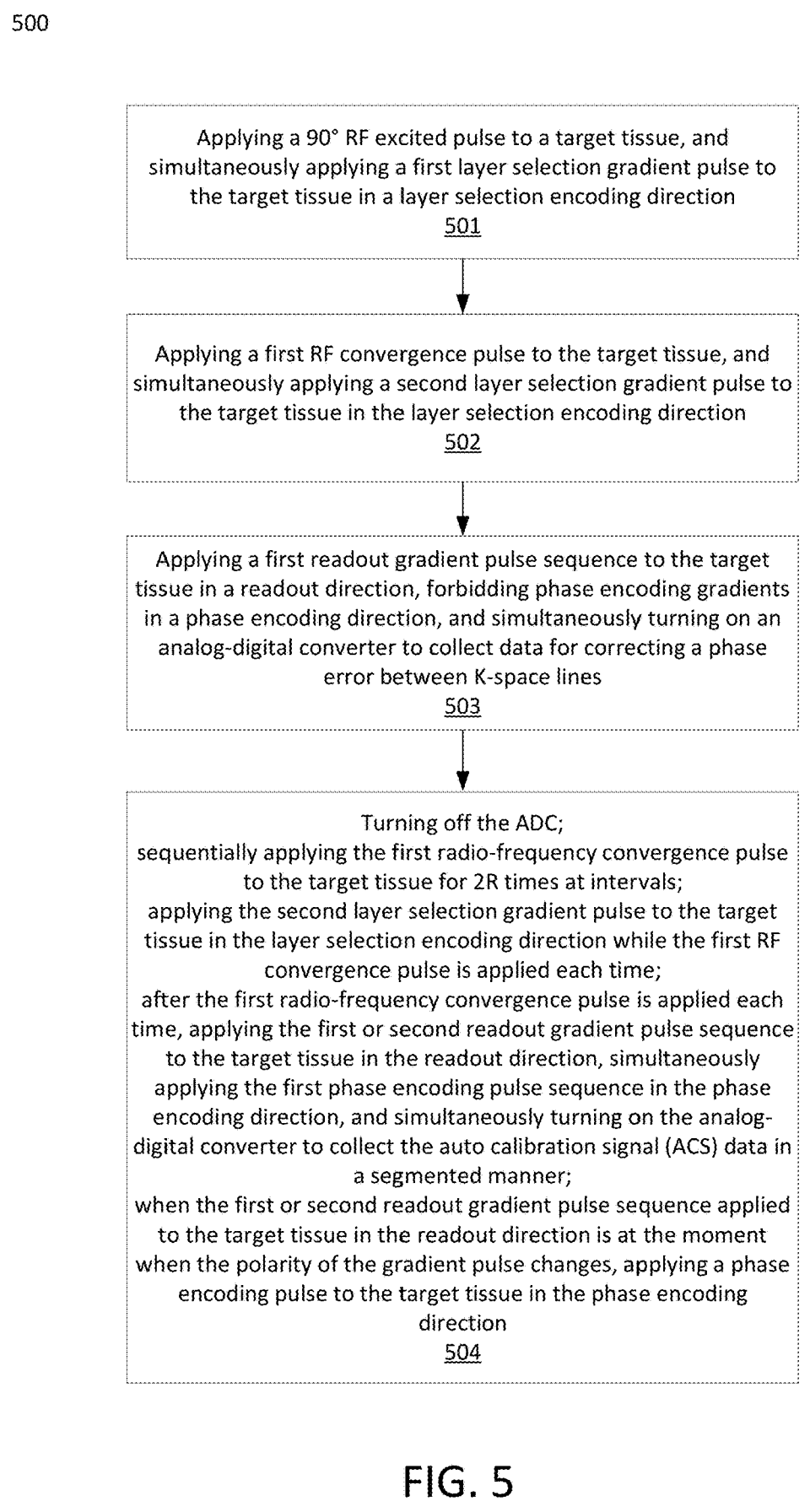

Applying a 90° RF excited pulse to a target tissue, and simultaneously applying a first layer selection gradient pulse to the target tissue in a layer selection encoding direction
501

Applying a first RF convergence pulse to the target tissue, and simultaneously applying a second layer selection gradient pulse to the target tissue in the layer selection encoding direction
502

Applying a first readout gradient pulse sequence to the target tissue in a readout direction, forbidding phase encoding gradients in a phase encoding direction, and simultaneously turning on an analog-digital converter to collect data for correcting a phase error between K-space lines
503

Turning off the ADC;
sequentially applying the first radio-frequency convergence pulse to the target tissue for 2R times at intervals;
applying the second layer selection gradient pulse to the target tissue in the layer selection encoding direction while the first RF convergence pulse is applied each time;
after the first radio-frequency convergence pulse is applied each time, applying the first or second readout gradient pulse sequence to the target tissue in the readout direction, simultaneously applying the first phase encoding pulse sequence in the phase encoding direction, and simultaneously turning on the analog-digital converter to collect the auto calibration signal (ACS) data in a segmented manner;
when the first or second readout gradient pulse sequence applied to the target tissue in the readout direction is at the moment when the polarity of the gradient pulse changes, applying a phase encoding pulse to the target tissue in the phase encoding direction
504

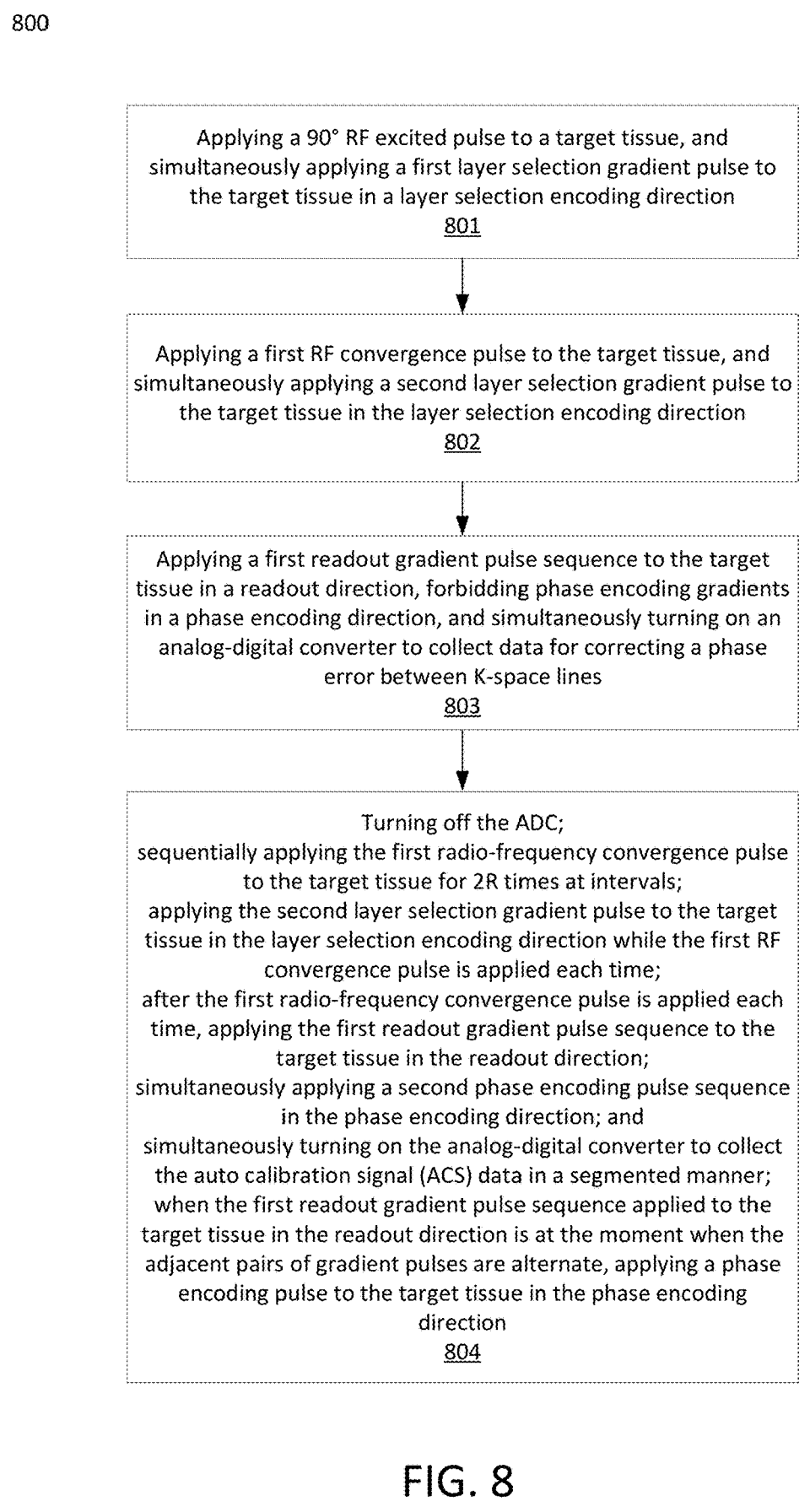

Applying a 90° RF excited pulse to a target tissue, and simultaneously applying a first layer selection gradient pulse to the target tissue in a layer selection encoding direction
801

↓

Applying a first RF convergence pulse to the target tissue, and simultaneously applying a second layer selection gradient pulse to the target tissue in the layer selection encoding direction
802

↓

Applying a first readout gradient pulse sequence to the target tissue in a readout direction, forbidding phase encoding gradients in a phase encoding direction, and simultaneously turning on an analog-digital converter to collect data for correcting a phase error between K-space lines
803

↓

Turning off the ADC;
sequentially applying the first radio-frequency convergence pulse to the target tissue for 2R times at intervals;
applying the second layer selection gradient pulse to the target tissue in the layer selection encoding direction while the first RF convergence pulse is applied each time;
after the first radio-frequency convergence pulse is applied each time, applying the first readout gradient pulse sequence to the target tissue in the readout direction;
simultaneously applying a second phase encoding pulse sequence in the phase encoding direction; and
simultaneously turning on the analog-digital converter to collect the auto calibration signal (ACS) data in a segmented manner;
when the first readout gradient pulse sequence applied to the target tissue in the readout direction is at the moment when the adjacent pairs of gradient pulses are alternate, applying a phase encoding pulse to the target tissue in the phase encoding direction
804

FIG. 8

EPI DATA CORRECTION METHOD AND DEVICE AND MRI SYSTEM

CROSS-REFERENCE TO RELATED APPLICATIONS

The present application claims priority to and the benefit of is China Patent Application no. CN 202310330106.7, filed Mar. 27, 2023, the contents of which are incorporated herein by reference in their entirety.

TECHNICAL FIELD

The present disclosure relates to the technical field of magnetic resonance imaging (MRI), in particular to an echo planar imaging (EPI) scanning method and device and an MRI system.

BACKGROUND

EPI is commonly used for functional activities, diffusion and MRI perfusion. EPI is often subjected to image blur caused by a long echo sequence length, Nyquist artifacts caused by the phase error associated with alternate positive and negative gradient acquisition, and geometric distortion caused by phase accumulation associated with off resonance. Image blur and distortion of accelerated parallel imaging in the phase encoding (PE) direction can be reduced by reducing the echo sequence length and the effective echo interval. The generalized auto-calibrating partially parallel acquisition (GRAPPA) method is usually used to reconstruct under-sampled imaging data. Typical EPI scanning usually includes the collection of fully-sampled auto calibration signal (ACS) data at the beginning and the subsequent collection of the under-sampled imaging data.

For robust parallel imaging reconstruction, it is best to match geometric distortion between the ACS data and the imaging data. The traditional method is to obtain the fully-sampled ACS data, and the number of segments of the segmented EPI is equal to the in-layer phase direction acceleration factor R. The ACS data and the imaging data have the same effective echo interval to match geometric distortion. The re-sorting solution is to collect the 1st segment of each layer firstly, then collect the 2nd segment of each layer, then collect the 3rd segment of each layer and so on to maintain a stable state of longitudinal magnetization. The time interval between the 1st segment and the last segment of the same layer is (R−1)*TR, and TR is time repetition. Usually, the ACS data of each segment can be collected at different stages of motion (such as physiological movement including breathing or heartbeat or overall movement of uncooperative patients). Uneven B0 shift in space due to movement may cause different phase shifts between the ACS data of different segments. The discontinuity generated on the ACS data of different segments will affect GRAPPA nuclear training, and then the generated nucleus will transmit artifacts and noise to the final accelerated image reconstruction.

A possible solution is to use another rapid collection, such as fast low angle shot (FLASH) collection, to replace the EPI collection of the ACS data, and the rapid collection is not sensitive to the dynamic B0 effect and Nyquist artifacts. However, geometric distortion mismatches between the ACS data collected by using the FLASH and accelerated EPI data; and therefore, the FLASH collection can only be used in the EPI collection scene with low susceptibility distortion.

Moreover, using the FLASH to collect the ACS data is incompatible with the dual-polarity GRAPPA (DPG) method, and the DPG method is proposed recently to reduce Nyquist artifacts caused by nonlinear phase difference between the data collected by EPI readout gradients with alternate polarities. This is because the DPG method requires that the readout gradients of the ACS data and the imaging data have the same shape, but the requirement cannot be fully satisfied when the ACS data are collected by using the FLASH.

The ACS segments are re-sorted by using a fast low-angle excitation echo-planar technique (FLEET) so as to continuously obtain segments within any given range. Therefore, the sensibility to the phase error between the segments is reduced by using the FLEET to collect the ACS data, so that the error caused by movement or dynamic B0 changes is reduced.

However, there are still limitations in using the FLEET to collect the ACS data. Although the segments in a layer are collected continuously in time, it may still be affected by large movement. In addition, a free induction decay (FID) signal will be obtained when the ACS data are collected by using the FLEET, which may be affected by the unevenness of a static B0 field. In an area with high B0 unevenness, significant phase error accumulation or even signal loss may occur, which reduces the quality of the ACS data.

SUMMARY

In view of this, on one hand, the example of the present disclosure provides an EPI scanning method and device to improve the quality of collected ACS data; and on the other hand, the example of the present disclosure provides an MRI system to improve the quality of the collected ACS data.

An echo planar imaging (EPI) scanning method, comprising:

- in a single excited EPI scanning process, firstly, applying a 90° radio-frequency excited pulse to a target tissue, and simultaneously applying a first layer selection gradient pulse to the target tissue in a layer selection encoding direction;
- after the radio-frequency excited pulse is applied, applying a first radio-frequency convergence pulse to the target tissue, and simultaneously applying a second layer selection gradient pulse to the target tissue in the layer selection encoding direction;
- after the first radio-frequency convergence pulse is applied, applying a first readout gradient pulse sequence to the target tissue in a readout direction, forbidding phase encoding gradients in a phase encoding direction, and simultaneously turning on an analog-digital converter to collect data for correcting a phase error between k-space lines; and
- after the first readout gradient pulse sequence is applied, turning off the analog-digital converter, sequentially applying the first radio-frequency convergence pulse to the target tissue for R times at intervals, and applying the second layer selection gradient pulse to the target tissue in the layer selection encoding direction while the first radio-frequency convergence pulse is applied each time; after the first radio-frequency convergence pulse is applied each time, applying the first readout gradient pulse sequence to the target tissue in the readout direction, simultaneously applying a first phase encoding pulse sequence in the phase encoding direction, and simultaneously turning on the analog-digital converter to collect auto calibration signal (ACS) data in a segmented manner, where R is an in-layer phase direction acceleration factor, and the first readout gradient pulse sequence is formed by a plurality of pairs of gradient pulses with opposite polarities; and when the first readout gradient pulse sequence applied to the target tissue in the readout direction is at the moment when the polarity of the gradient pulse changes, applying a phase encoding pulse to the target tissue in the phase encoding direction.

After simultaneously turning on the analog-digital converter to collect ACS data in a segmented manner, the method further comprises:

re-sorting the ACS data collected in a segmented manner to obtain ACS data in the k-space, where the re-sorting principle is that: a corresponding line number of the ACS data collected by the pith readout gradient pulse in any segment p in the k-space is R*(pi−1)+p, where 1≤p≤R and pi≥1.

After the radio-frequency excited pulse is applied and before the first radio-frequency convergence pulse is applied to the target tissue, the method further comprises:

sequentially applying the first radio-frequency convergence pulse to the target tissue for preset times at intervals; applying the second layer selection gradient pulse to the target tissue in the layer selection encoding direction while the first radio-frequency convergence pulse is applied each time; and after the first radio-frequency convergence pulse is applied each time, applying the first readout gradient pulse sequence to the target tissue in the readout direction, forbidding the phase encoding gradients in the phase encoding direction, and simultaneously forbidding (e.g. turning off) the analog-digital converter.

An echo planar imaging (EPI) scanning method, comprising:

in the single excited EPI scanning process, firstly, applying the 90° radio-frequency excited pulse to the target tissue, and simultaneously applying the first layer selection gradient pulse to the target tissue in the layer selection encoding direction;

after the radio-frequency excited pulse is applied, applying the first radio-frequency convergence pulse to the target tissue, and simultaneously applying the second layer selection gradient pulse to the target tissue in the layer selection encoding direction;

after the first radio-frequency convergence pulse is applied, applying the first readout gradient pulse sequence to the target tissue in the readout direction, forbidding the phase encoding gradients in the phase encoding direction, and simultaneously turning on the analog-digital converter to collect the data for correcting the phase error between the k-space lines; and after the first readout gradient pulse sequence is applied, turning off the analog-digital converter, sequentially applying the first radio-frequency convergence pulse to the target tissue for 2R times at intervals, and applying the second layer selection gradient pulse to the target tissue in the layer selection encoding direction while the first radio-frequency convergence pulse is applied each time; after the first radio-frequency convergence pulse is applied each time, applying the first or second readout gradient pulse sequence to the target tissue in the readout direction, simultaneously applying the first phase encoding pulse sequence in the phase encoding direction, and simultaneously turning on the analog-digital converter to collect the auto calibration signal (ACS) data in a segmented manner, where R is the in-layer phase direction acceleration factor, the first readout gradient pulse sequence is applied to the target tissue at odd-numbered times in the 2R times, the second readout gradient pulse sequence is applied to the target tissue at even-numbered times in the 2R times, each of the first and second readout gradient pulse sequence is formed by a plurality of pairs of gradient pulses with opposite polarities, and the polarity of the first readout gradient pulse sequence is opposite to that of the second readout gradient pulse sequence; and when the first or second readout gradient pulse sequence applied to the target tissue in the readout direction is at the moment when the polarity of the gradient pulse changes, applying a phase encoding pulse to the target tissue in the phase encoding direction.

After simultaneously turning on the analog-digital converter to collect ACS data in a segmented manner, the method further comprises:

re-sorting the ACS data collected in a segmented manner to obtain ACS data in a positive readout gradient k-space and ACS data in a negative readout gradient k-space, where the re-sorting principle is that:

a corresponding line number of the ACS data collected by the lith positive readout gradient pulse in any odd-numbered segment 1 in the positive readout gradient k-space is 2R*(li−1)+(l+1)/2, a corresponding line number of the ACS data collected by the ljth negative readout gradient pulse in any odd-numbered segment 1 in the negative readout gradient k-space is 2R*lj−R+(l+1)/2, a corresponding line number of the ACS data collected by the rjth negative readout gradient pulse in any even-numbered segment r in the negative readout gradient k-space is 2R*(rj−1)+r/2, and a corresponding line number of the ACS data collected by the rith positive readout gradient pulse in any even-numbered segment r in the positive readout gradient k-space is 2R*ri−R+r/2, where 1≤l≤2R−1, 2≤r≤2R, li≥1, lj≥1, rj≥1 and ri≥1.

After the radio-frequency excited pulse is applied and before the first radio-frequency convergence pulse is applied to the target tissue, the method further comprises:

sequentially applying the first radio-frequency convergence pulse to the target tissue for preset times at intervals; applying the second layer selection gradient pulse to the target tissue in the layer selection encoding direction while the first radio-frequency convergence pulse is applied each time; and after the first radio-frequency convergence pulse is applied each time, applying the first readout gradient pulse sequence to the target tissue in the readout direction, forbidding the phase encoding gradients in the phase encoding direction, and simultaneously forbidding the analog-digital converter.

An echo planar imaging (EPI) scanning method, comprising:

in the single excited EPI scanning process, firstly, applying the 90° radio-frequency excited pulse to the target tissue, and simultaneously applying the first layer selection gradient pulse to the target tissue in the layer selection encoding direction;

after the radio-frequency excited pulse is applied, applying the first radio-frequency convergence pulse to the target tissue, and simultaneously applying the second layer selection gradient pulse to the target tissue in the layer selection encoding direction;

after the first radio-frequency convergence pulse is applied, applying the first readout gradient pulse sequence to the target tissue in the readout direction, forbidding phase encoding gradients in the phase encoding direction, and simultaneously turning on the analog-digital converter to collect the data for correcting the phase error between the k-space lines; and after the first readout gradient pulse sequence is applied, turning off the analog-digital converter, sequentially applying the first radio-frequency convergence pulse to the target tissue for 2R times at intervals, and applying the second layer selection gradient pulse to the target tissue in the layer selection encoding direction while the first radio-frequency convergence pulse is applied each time; after the first radio-frequency convergence pulse is applied each time, applying the first readout gradient pulse sequence to the target tissue in the readout direction, simultaneously applying a second phase encoding pulse sequence in the phase encoding direction, and simultaneously turning on the analog-digital converter to collect the auto calibration signal (ACS) data in a segmented manner, where R is the in-layer phase direction acceleration factor, and the first readout gradient pulse sequence is formed by a plurality of pairs of gradient pulses with opposite polarities; and when the first readout gradient pulse sequence applied to the target tissue in the readout direction is at the moment when the adjacent pairs of gradient pulses are alternate, applying a phase encoding pulse to the target tissue in the phase encoding direction.

After simultaneously turning on the analog-digital converter to collect ACS data in a segmented manner, the method further comprises:

re-sorting the ACS data collected in a segmented manner to obtain the ACS data in the k-space, where the re-sorting principle is that:

a corresponding line number of the ACS data collected by the tith positive readout gradient pulse in any segment t in a positive readout gradient k-space is $2R*(ti-1)+t$, and a corresponding line number of the ACS data collected by the tjth negative readout gradient pulse in any segment 1 in a negative readout gradient k-space is $2R*(tj-1)+t$, where $1 \leq t \leq 2R$, $ti \geq 1$ and $tj \geq 1$.

After the radio-frequency excited pulse is applied and before the first radio-frequency convergence pulse is applied to the target tissue, the method further comprises:

sequentially applying the first radio-frequency convergence pulse to the target tissue for preset times at intervals; applying the second layer selection gradient pulse to the target tissue in the layer selection encoding direction while the first radio-frequency convergence pulse is applied each time; and after the first radio-frequency convergence pulse is applied each time, applying the first readout gradient pulse sequence to the target tissue in the readout direction, forbidding the phase encoding gradients in the phase encoding direction, and simultaneously forbidding the analog-digital converter.

An echo planar imaging (EPI) scanning device, comprising:

a first data collection module used for in the single excited EPI scanning process, firstly, applying the 90° radio-frequency excited pulse to the target tissue, and simultaneously applying the first layer selection gradient pulse to the target tissue in the layer selection encoding direction; after the radio-frequency excited pulse is applied, applying the first radio-frequency convergence pulse to the target tissue, and simultaneously applying the second layer selection gradient pulse to the target tissue in the layer selection encoding direction; and after the first radio-frequency convergence pulse is applied, applying the first readout gradient pulse sequence to the target tissue in the readout direction, forbidding the phase encoding gradients in the phase encoding direction, and simultaneously turning on the analog-digital converter to collect the data for correcting the phase error between the k-space lines; and a second data collection module used for after the first readout gradient pulse sequence is applied, turning off the analog-digital converter, sequentially applying the first radio-frequency convergence pulse to the target tissue for R times at intervals, and applying the second layer selection gradient pulse to the target tissue in the layer selection encoding direction while the first radio-frequency convergence pulse is applied each time; after the first radio-frequency convergence pulse is applied each time, applying the first readout gradient pulse sequence to the target tissue in the readout direction, simultaneously applying the first phase encoding pulse sequence in the phase encoding direction, and simultaneously turning on the analog-digital converter to collect the auto calibration signal (ACS) data in a segmented manner, where R is the in-layer phase direction acceleration factor, and the first readout gradient pulse sequence is formed by a plurality of pairs of gradient pulses with opposite polarities; and when the first readout gradient pulse sequence applied to the target tissue in the readout direction is at the moment when the polarity of the gradient pulse changes, applying a phase encoding pulse to the target tissue in the phase encoding direction.

After simultaneously turning on the analog-digital converter to collect ACS data in a segmented manner, the second data collection module is further used for:

re-sorting the ACS data collected in a segmented manner to obtain the ACS data in the k-space, where the re-sorting principle is that: a corresponding line number of the collected ACS data in the pith line in any segment p in the k-space after re-sorting is $R*(pi-1)+p$, where $1 \leq p \leq R$ and $pi \geq 1$.

After the radio-frequency excited pulse is applied and before the first radio-frequency convergence pulse is applied to the target tissue, the first data collection module is further used for:

sequentially applying the first radio-frequency convergence pulse to the target tissue for preset times at intervals; applying the second layer selection gradient pulse to the target tissue in the layer selection encoding direction while the first radio-frequency convergence pulse is applied each time; and after the first radio-frequency convergence pulse is applied each time, applying the first readout gradient pulse sequence to the target tissue in the readout direction, forbidding the phase encoding gradients in the phase encoding direction, and simultaneously forbidding the analog-digital converter.

An echo planar imaging (EPI) scanning device, comprising:

a third data collection module used for in the single excited EPI scanning process, firstly, applying the 90° radio-frequency excited pulse to the target tissue, and simultaneously applying the first layer selection gradient pulse to the target tissue in the layer selection encoding direction; after the radio-frequency excited pulse is applied, applying the first radio-frequency convergence pulse to the target tissue, and simultaneously applying the second layer selection gradient pulse to the target tissue in the layer selection encoding direction; and after the first radio-frequency convergence pulse is applied, applying the first readout gradient pulse sequence to the target tissue in the readout direction, forbidding the phase encoding gradients in the phase encoding direction, and simultaneously turning on the analog-digital converter to collect the data for correcting the phase error between the k-space lines; and a fourth data collection module used for after the first readout gradient pulse sequence is applied, turning off the analog-digital converter, sequentially applying the first radio-frequency convergence pulse to the target tissue for 2R times at intervals, and applying the second layer selection gradient pulse to the target tissue in the layer selection encoding direction while the first radio-frequency convergence pulse is applied each time; after the first radio-frequency convergence pulse is applied each time, applying the first or second readout gradient pulse sequence to the target tissue in the readout direction, simultaneously applying the first phase encoding pulse sequence in the phase encoding direction, and simultaneously turning on the analog-digital converter to collect the auto calibration signal (ACS) data in a segmented manner, where R is the in-layer phase direction acceleration factor, the first readout gradient pulse sequence is applied to the target tissue at odd-numbered times in the 2R times, the second readout gradient pulse sequence is applied to the target tissue at even-numbered times in the 2R times, each of the first and second readout gradient pulse sequence is formed by a plurality of pairs of gradient pulses with opposite polarities, and the polarity of the first readout gradient pulse sequence is opposite to that of the second readout gradient pulse sequence; and when the first or second readout gradient pulse sequence applied to the target tissue in the readout direction is at the moment when the polarity of the gradient pulse changes, applying a phase encoding pulse to the target tissue in the phase encoding direction.

After simultaneously turning on the analog-digital converter to collect ACS data in a segmented manner, the fourth data collection module is further used for:

re-sorting the ACS data collected in a segmented manner to obtain the ACS data in the positive readout gradient k-space and the ACS data in the negative readout gradient k-space, where the re-sorting principle is that:

a corresponding line number of the ACS data collected by the lith positive readout gradient pulse in any odd-numbered segment 1 in the positive readout gradient k-space is $2R*(li-1)+(l+1)/2$, a corresponding line number of the ACS data collected by the ljth negative readout gradient pulse in any odd-numbered segment 1 in the negative readout gradient k-space is $2R*lj-R+(l+1)/2$, a corresponding line number of the ACS data collected by the rjth negative readout gradient pulse in any even-numbered segment r in the negative readout gradient k-space is $2R*(rj-1)+r/2$, and a corresponding line number of the ACS data collected by the rith positive readout gradient pulse in any even-numbered segment r in the positive readout gradient k-space is $2R*ri-R+r/2$, where $1 \le l \le 2R-1$, $2 \le r \le 2R$, $li \ge 1$, $lj \ge 1$, $rj \ge 1$ and $ri \ge 1$.

After the radio-frequency excited pulse is applied and before the first radio-frequency convergence pulse is applied to the target tissue, the third data collection module is further used for:

sequentially applying the first radio-frequency convergence pulse to the target tissue for preset times at intervals; applying the second layer selection gradient pulse to the target tissue in the layer selection encoding direction while the first radio-frequency convergence pulse is applied each time; and after the first radio-frequency convergence pulse is applied each time, applying the first readout gradient pulse sequence to the target tissue in the readout direction, forbidding the phase encoding gradients in the phase encoding direction, and simultaneously forbidding the analog-digital converter.

An echo planar imaging (EPI) scanning device, comprising:

a fifth data collection module used for in the single excited EPI scanning process, firstly, applying the 90° radio-frequency excited pulse to the target tissue, and simultaneously applying the first layer selection gradient pulse to the target tissue in the layer selection encoding direction; after the radio-frequency excited pulse is applied, applying the first radio-frequency convergence pulse to the target tissue, and simultaneously applying the second layer selection gradient pulse to the target tissue in the layer selection encoding direction; and after the first radio-frequency convergence pulse is applied, applying the first readout gradient pulse sequence to the target tissue in the readout direction, forbidding the phase encoding gradients in the phase encoding direction, and simultaneously turning on the analog-digital converter to collect the data for correcting the phase error between the k-space lines; and a sixth data collection module used for after the first readout gradient pulse sequence is applied, turning off the analog-digital converter, sequentially applying the first radio-frequency convergence pulse to the target tissue for 2R times at intervals, and applying the second layer selection gradient pulse to the target tissue in the layer selection encoding direction while the first radio-frequency convergence pulse is applied each time; after the first radio-frequency convergence pulse is applied each time, applying the first readout gradient pulse sequence to the target tissue in the readout direction, simultaneously applying a second phase encoding pulse sequence in the phase encoding direction, and simultaneously turning on the analog-digital converter to collect the auto calibration signal (ACS) data in a segmented manner, where R is the in-layer phase direction acceleration factor, and the first readout gradient pulse sequence is formed by a plurality of pairs of gradient pulses with opposite polarities; and when the first readout gradient pulse sequence applied to the target tissue in the readout direction is at the moment when the adjacent pairs of gradient pulses are alternate, applying a phase encoding pulse to the target tissue in the phase encoding direction.

After simultaneously turning on the analog-digital converter to collect ACS data in a segmented manner, the sixth data collection module is further used for:

re-sorting the ACS data collected in a segmented manner to obtain the ACS data in the k-space, where the re-sorting principle is that:

a corresponding line number of the ACS data collected by the tith positive readout gradient pulse in any segment t in a positive readout gradient k-space is 2R*(ti−1)+t, and a corresponding line number of the ACS data collected by the tjth negative readout gradient pulse in any segment 1 in a negative readout gradient k-space is 2R*(tj−1)+t, where 1≤t≤2R, ti≥1 and tj≥1.

After the radio-frequency excited pulse is applied and before the first radio-frequency convergence pulse is applied to the target tissue, the fifth data collection module is further used for:

sequentially applying the first radio-frequency convergence pulse to the target tissue for preset times at intervals; applying the second layer selection gradient pulse to the target tissue in the layer selection encoding direction while the first radio-frequency convergence pulse is applied each time; and after the first radio-frequency convergence pulse is applied each time, applying the first readout gradient pulse sequence to the target tissue in the readout direction, forbidding the phase encoding gradients in the phase encoding direction, and simultaneously forbidding the analog-digital converter.

A magnetic resonance imaging (MRI) system, comprising any one of the echo planar imaging (EPI) scanning devices as described above.

According to the example of the present disclosure, the ACS data of all the segments are collected in one excitation, therefore, the sensibility of the ACS data of all the segments to movement is reduced, the phase error between the ACS data of all the segments is reduced, and the quality of the ACS data is improved, thereby reducing the influence of the movement on a final reconstructed image and reducing Nyquist ghosting in the final reconstructed image. The data for correcting the phase error between the k-space lines and the ACS data of all the segments are collected by using the same readout gradient pulse sequence, so that the deformation is consistent between the ACS data and the imaging data, thereby reducing the Nyquist ghosting in the final reconstructed image. The ACS data of the segments are collected by a plurality of spin echoes generated in one excitation, so that the collected ACS data are not sensitive to the B0 unevenness. When high B0 unevenness occurs, the quality of the final reconstructed image is more stable, and the signal noise ratio (SNR) of the reconstructed image is improved.

BRIEF DESCRIPTION OF THE DRAWINGS

In order to clearly understand the above and other features and advantages of the present disclosure by those ordinarily skilled in the art, the preferred example of the present disclosure will be described in detail with reference to drawings below, and in the drawings:

FIG. 1 is a flow diagram of an EPI scanning method provided by one example of the present disclosure.

FIG. 5 is a flow diagram of an EPI scanning method provided by another example of the present disclosure.

FIG. 8 is a flow diagram of an EPI scanning method provided by yet another example of the present disclosure.

Figures 2, 3:
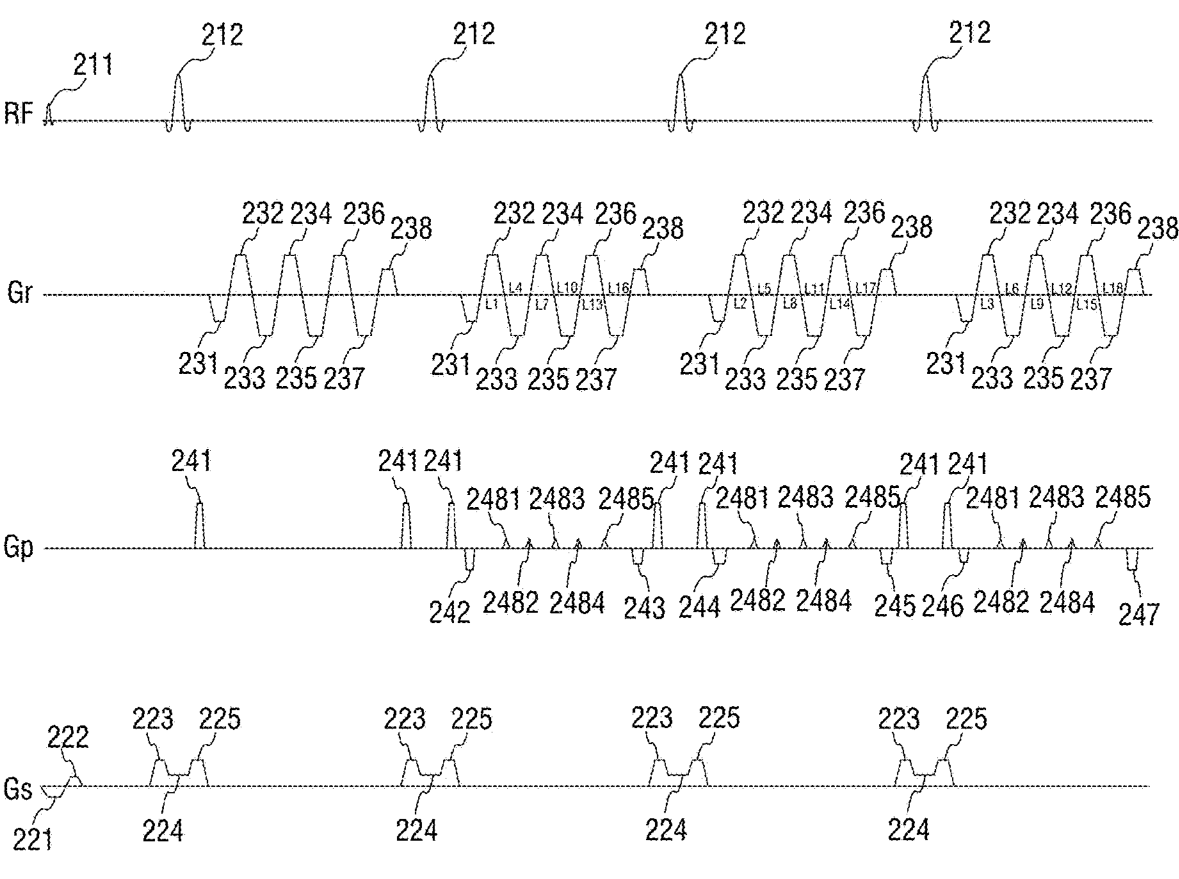
FIG. 2 is a schematic diagram of an EPI scanning process for collecting ACS data in one application example of the present disclosure.
FIG. 3 is a representation diagram of a k-space after the ACS data collected in the EPI scanning process shown in FIG. 2 are re-sorted.

The reference numerals are as follows:

| Number | Meaning |
|---|---|
| 101-104 | Block/step |
| 211 | 90° radio-frequency excited pulse |
| 212 | First radio-frequency convergence pulse |
| 221 | First layer selection gradient pulse |
| 222 | Convergence gradient pulse for layer selection gradient |
| 223 and 225 | Damage gradient pulse |
| 224 | Second layer selection gradient pulse |
| 231 | Pre-dispersed phase gradient pulse in the readout direction |
| 232-237 | First readout gradient pulse sequence |
| 238 | Phase convergence gradient pulse in the readout direction |
| 241 | Damage gradient |
| 242, 244 and 246 | Pre-dispersed phase gradient pulse in the phase encoding direction |
| 243, 245 and 247 | Phase convergence gradient pulse in the phase encoding direction |
| 2481-2485 | First phase encoding gradient pulse sequence |
| 41 | EPI scanning stage corresponding to a plurality of spin echoes at the beginning |
| 501-504 | Block/Step |
| 611 | 90° radio-frequency excited pulse |
| 612 | First radio-frequency convergence pulse |
| 621 | First layer selection gradient pulse |
| 622 | Convergence gradient pulse for layer selection gradient |
| 623 and 625 | Damage gradient pulse |
| 624 | Second layer selection gradient pulse |

-continued

| Number | Meaning |
|---|---|
| 6311 and 6321 | Pre-dispersed phase gradient pulse in the readout direction |
| 6312-6317 | First readout gradient pulse sequence |
| 6322-6327 | Second readout gradient pulse sequence |
| 6318 and 6328 | Phase convergence gradient pulse in the readout direction |
| 641 | Damage gradient pulse |
| 642, 644 and 646 | Pre-dispersed phase gradient pulse in the phase encoding direction |
| 6481-6485 | First phase encoding gradient pulse sequence |
| 643, 645 and 647 | Phase convergence gradient pulse in the phase encoding direction |
| 610 | EPI scanning stage corresponding to 6 first radio-frequency convergence pulses |
| 71 | Positive readout gradient k-space |
| 72 | Negative readout gradient k-space |
| 801-804 | Block/Step |
| 911 | 90° radio-frequency excited pulse |
| 912 | First radio-frequency convergence pulse |
| 921 | First layer selection gradient pulse |
| 922 | Convergence gradient pulse for layer selection gradient |
| 923 and 925 | Damage gradient pulse |
| 924 | Second layer selection gradient pulse |
| 931 | Pre-dispersed phase gradient pulse in the readout direction |
| 932-937 | First readout gradient pulse sequence |
| 938 | Phase convergence gradient pulse in the readout direction |
| 941 | Damage gradient pulse |
| 942, 944 and 946 | Pre-dispersed phase gradient pulse in the phase encoding direction |
| 948-949 | Second phase encoding gradient pulse sequence |
| 943, 945 and 947 | Phase convergence gradient pulse in the phase encoding direction |
| 910 | EPI scanning stage corresponding to 6 first radio-frequency convergence pulses |
| 101 | Positive readout gradient k-space |
| 102 | Negative readout gradient k-space |
| 1100 | EPI scanning device provided by one example of the present disclosure |
| 1110 | First data collection module |
| 1120 | Second data collection module |
| 1200 | EPI scanning device provided by another example of the present disclosure |
| 1210 | Third data collection module |
| 1220 | Fourth data collection module |
| 1300 | EPI scanning device provided by yet another example of the present disclosure |
| 1310 | Fifth data collection module |
| 1320 | Sixth data collection module |

DETAILED DESCRIPTION OF THE DISCLOSURE

In order to clearly understand the objectives, technical solutions and advantages of the present disclosure, the present disclosure will be further described in detail with reference to the examples below.

FIG. 1 is a flow diagram of an EPI scanning method provided by one example of the present disclosure. The EPI scanning method includes the specific steps as follows:

step 101: in a single excited EPI scanning process, firstly, applying a 90° radio-frequency excited pulse to a target tissue, and simultaneously applying a first layer selection gradient pulse to the target tissue in a layer selection encoding direction;

step 102: after the radio-frequency excited pulse is applied, applying a first radio-frequency convergence pulse to the target tissue, and simultaneously applying a second layer selection gradient pulse to the target tissue in the layer selection encoding direction;

step 103: after the first radio-frequency convergence pulse is applied, applying a first readout gradient pulse sequence to the target tissue in a readout direction, forbidding phase encoding gradients in a phase encoding direction, and simultaneously turning on an analog-digital converter to collect data for correcting a phase error between k-space lines; and step 104: after the first readout gradient pulse sequence is applied, turning off the analog-digital converter, sequentially applying the first radio-frequency convergence pulse to the target tissue for R times at intervals, and applying the second layer selection gradient pulse to the target tissue in the layer selection encoding direction while the first radio-frequency convergence pulse is applied each time; after the first radio-frequency convergence pulse is applied each time, applying the first readout gradient pulse sequence to the target tissue in the readout direction, simultaneously applying a first phase encoding pulse sequence in the phase encoding direction, and simultaneously turning on the analog-digital converter to collect auto calibration signal (ACS) data in a segmented manner, where R is an in-layer phase direction acceleration factor, and the first readout gradient pulse sequence is formed by a plurality of pairs of gradient pulses with opposite polarities; and when the first readout gradient pulse sequence applied to the target tissue in the readout direction is at the moment when the polarity of the gradient pulse changes, applying a phase encoding pulse to the target tissue in the phase encoding direction.

The first readout gradient pulse sequence can be formed by a plurality of pairs of positive and negative gradient pulses or a plurality of pairs of negative and positive gradient pulses.

The above example has the following beneficial technical effects:

I. The ACS data of all the segments are collected in one excitation, therefore, the sensibility of the ACS data of all the segments to movement is reduced, the phase error between the ACS data of all the segments is reduced, and the quality of the ACS data is improved, thereby reducing the influence of the movement on the final reconstructed image and reducing the Nyquist ghosting in the final reconstructed image.

II. The data for correcting the phase error between the k-space lines and the ACS data of all the segments are collected by using the same readout gradient pulse sequence, so that the deformation is consistent between the ACS data and the imaging data, thereby reducing the Nyquist ghosting in the final reconstructed image.

III. The ACS data of the segments are collected by a plurality of spin echoes generated in one excitation, so that the collected ACS data are not sensitive to the B0 unevenness. When high B0 unevenness occurs, the quality of the final reconstructed image is more stable, and the signal noise ratio (SNR) of the reconstructed image is improved.

FIG. 2 is a schematic diagram of an EPI scanning process for collecting the ACS data in one application example of the present disclosure. An EPI scanning sequence may be a turbo gradient spin echo (TGSE) sequence, and in the present example, the in-layer phase direction acceleration factor R is equal to 3, where RF represents the radio-frequency pulse transmitted to the target tissue, where 211 represents the 90° radio-frequency excited pulse, and 212 represents the first radio-frequency convergence pulse;

Gs represents a gradient field applied to the target tissue in the layer selection encoding direction, where 221 represents the first layer selection gradient pulse, 222 represents the convergence gradient pulse for the layer selection gradient, 223 and 225 represent the damage gradient pulse, and 224 represents the second layer selection gradient pulse;

Gr represents a gradient field applied to the target tissue in the readout direction, where 231 represents the pre-dispersed phase gradient pulse in the readout direction, 232-237 represent the first readout gradient pulse sequence, and 238 represents the phase convergence gradient pulse in the readout direction; and Gp represents a gradient field applied to the target tissue in the phase encoding direction, where 241 represents the damage gradient pulse, 242, 244 and 246 represent the pre-dispersed phase gradient pulse in the phase encoding direction, 2481-2485 represent the first phase encoding gradient pulse sequence, and 243, 245 and 247 represent the phase convergence gradient pulse in the phase encoding direction.

In one optional example, after simultaneously turning on the analog-digital converter to collect ACS data in a segmented manner, the step 104 further includes: re-sorting the ACS data collected in a segmented manner to obtain the ACS data in the k-space, where the re-sorting principle is that: the corresponding line number of the collected ACS data in the pith line in any segment p in the k-space after re-sorting is R*(pi−1)+p, where 1≤p≤R and pi≥1.

After the ACS data in the k-space are obtained, the data for correcting the phase error between the k-space lines in the step 103 can be used for correcting the phase error between the k-space lines (i.e., between the ACS data in different lines); then the ACS data with the corrected phase error are fit to obtain a GRAPPA nucleus in a GRAPPA-based reconstruction method; and when imaging data are collected in the EPI scanning process, the imaging data can be reconstructed by using the GRAPPA nucleus to obtain a reconstructed image.

FIG. 3 is a representation diagram of a k-space after the ACS data collected in the EPI scanning process shown in FIG. 2 are re-sorted. As shown in FIG. 3, the corresponding line number of the ACS data of the segment 1 collected by the first spin echo in FIG. 2 in the k-space is L1, L4, L7, L10, L13 and L16 in sequence, the corresponding line number of the ACS data of the segment 2 collected by the second spin echo in the k-space is L2, L5, L8, L11, L14 and L17 in sequence, and the corresponding line number of the ACS data of the segment 3 collected by the third spin echo in the k-space is L3, L6, L9, L12, L15 and L18 in sequence. The final representation of the k-space of all the ACS data is shown in FIG. 3.

It is important to maintain roughly equal signal amplitude between the ACS data of the segments. Since the spin echoes generated at the beginning after one excitation have faster T2 attenuation, in order to reduce amplitude modulation between the ACS data of different segments, data collection may not be performed on a plurality of spin echoes generated at the beginning in practical application, specifically as follows:

in one optional example, after the radio-frequency excited pulse is applied and before the first radio-frequency convergence pulse is applied to the target tissue, the step 102 further includes: sequentially applying the first radio-frequency convergence pulse to the target tissue for preset times at intervals; applying the second layer selection gradient pulse to the target tissue in the layer selection encoding direction while the first radio-frequency convergence pulse is applied each time; and after the first radio-frequency convergence pulse is applied each time, applying the first readout gradient pulse sequence to the target tissue in the readout direction, forbidding the phase encoding gradients in the phase encoding direction, and simultaneously forbidding the analog-digital converter. The preset times may be 5 to 10 times.

Figure 4:
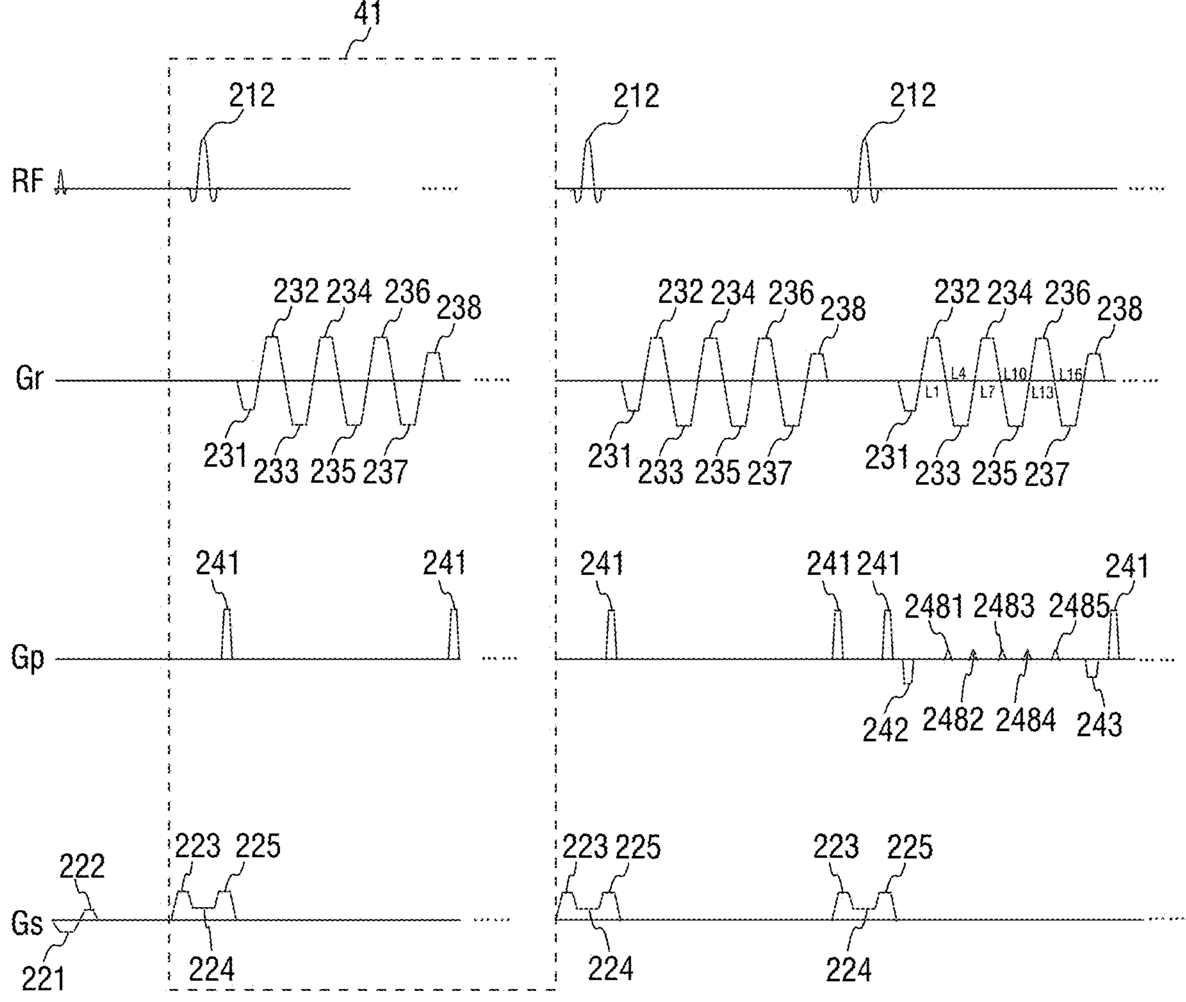
FIG. 4 is a schematic diagram of an EPI scanning process for collecting the ACS data in another application example of the present disclosure.

FIG. 4 is a schematic diagram of an EPI scanning process for collecting the ACS data in another application example of the present disclosure. The EPI scanning sequence may be the turbo gradient spin echo (TGSE) sequence, where RF represents the radio-frequency pulse transmitted to the target tissue, where 211 represents the 90° radio-frequency excited pulse, and 212 represents the first radio-frequency convergence pulse;

Gs represents a gradient field applied to the target tissue in the layer selection encoding direction, where 221 represents the first layer selection gradient pulse, 222 represents the convergence gradient pulse for the layer selection gradient, 223 and 225 represent the damage gradient pulse, and 224 represents the second layer selection gradient pulse;

Gr represents a gradient field applied to the target tissue in the readout direction, where 231 represents the pre-dispersed phase gradient pulse in the readout direction, 232-237 represent the first readout gradient pulse sequence, and 238 represents the phase convergence gradient pulse in the readout direction; and Gp represents a gradient field applied to the target tissue in the phase encoding direction, where 241 represents the damage gradient pulse, 242, 244 and 246 represent the pre-dispersed phase gradient pulse in the phase encoding direction, 2481-2485 represent the first phase encoding gradient pulse sequence, and 243, 245 and 247 represent the phase convergence gradient pulse in the phase encoding direction.

As shown in FIG. 4, data collection is not performed on the plurality of spin echoes at the beginning in a dotted box 41, i.e., the analog-digital converter is turned off.

FIG. 5 is a flow diagram of an EPI scanning method provided by another example of the present disclosure. The EPI scanning method includes the specific steps as follows:

step 501: in a single excited EPI scanning process, firstly, applying a 90° radio-frequency excited pulse to a target tissue, and simultaneously applying a first layer selection gradient pulse to the target tissue in a layer selection encoding direction;

step 502: after the radio-frequency excited pulse is applied, applying a first radio-frequency convergence pulse to the target tissue, and simultaneously applying a second layer selection gradient pulse to the target tissue in the layer selection encoding direction;

step 503: after the first radio-frequency convergence pulse is applied, applying a first readout gradient pulse sequence to the target tissue in a readout direction, forbidding phase encoding gradients in a phase encoding direction, and simultaneously turning on an analog-digital converter to collect data for correcting a phase error between k-space lines; and step 504: after the first readout gradient pulse sequence is applied, turning off the analog-digital converter, sequentially applying the first radio-frequency convergence pulse to the target tissue for 2R times at intervals, and applying the second layer selection gradient pulse to the target tissue in the layer selection encoding direction while the first radio-frequency convergence pulse is applied each time; after the first radio-frequency convergence pulse is applied each time, applying the first or second readout gradient pulse sequence to the target tissue in the readout direction, simultaneously applying the first phase encoding pulse sequence in the phase encoding direction, and simultaneously turning on the analog-digital converter to collect the auto calibration signal (ACS) data in a segmented manner, where R is the in-layer phase direction acceleration factor, the first readout gradient pulse sequence is applied to the target tissue at odd-numbered times in the 2R times, the second readout gradient pulse sequence is applied to the target tissue at even-numbered times in the 2R times, each of the first and second readout gradient pulse sequence is formed by a plurality of pairs of gradient pulses with opposite polarities, and the polarity of the first readout gradient pulse sequence is opposite to that of the second readout gradient pulse sequence; and when the first or second readout gradient pulse sequence applied to the target tissue in the readout direction is at the moment when the polarity of the gradient pulse changes, applying a phase encoding pulse to the target tissue in the phase encoding direction.

For example, when the first readout gradient pulse sequence is formed by a plurality of pairs of positive and negative gradient pulses, the second readout gradient pulse sequence is formed by a plurality of pairs of negative and positive gradient pulses; or when the first readout gradient pulse sequence is formed by a plurality of pairs of negative and positive gradient pulses, the second readout gradient pulse sequence is formed by a plurality of pairs of positive and negative gradient pulses.

The above example has the following beneficial technical effects:

I. The ACS data of all the segments are collected in one excitation, therefore, the sensibility of the ACS data of all the segments to movement is reduced, the phase error between the ACS data of all the segments is reduced, and the quality of the ACS data is improved, thereby reducing the influence of the movement on the final reconstructed image and reducing the Nyquist ghosting in the final reconstructed image.

II. The data for correcting the phase error between the k-space lines and the ACS data of all the segments are collected by using the same readout gradient pulse sequence, so that the deformation is consistent between the ACS data and the imaging data, thereby reducing the Nyquist ghosting in the final reconstructed image.

III. The ACS data of the segments are collected by a plurality of spin echoes generated in one excitation, so that the collected ACS data are not sensitive to the B0 unevenness. When high B0 unevenness occurs, the quality of the final reconstructed image is more stable, and the SNR of the reconstructed image is improved.

Figure 6:
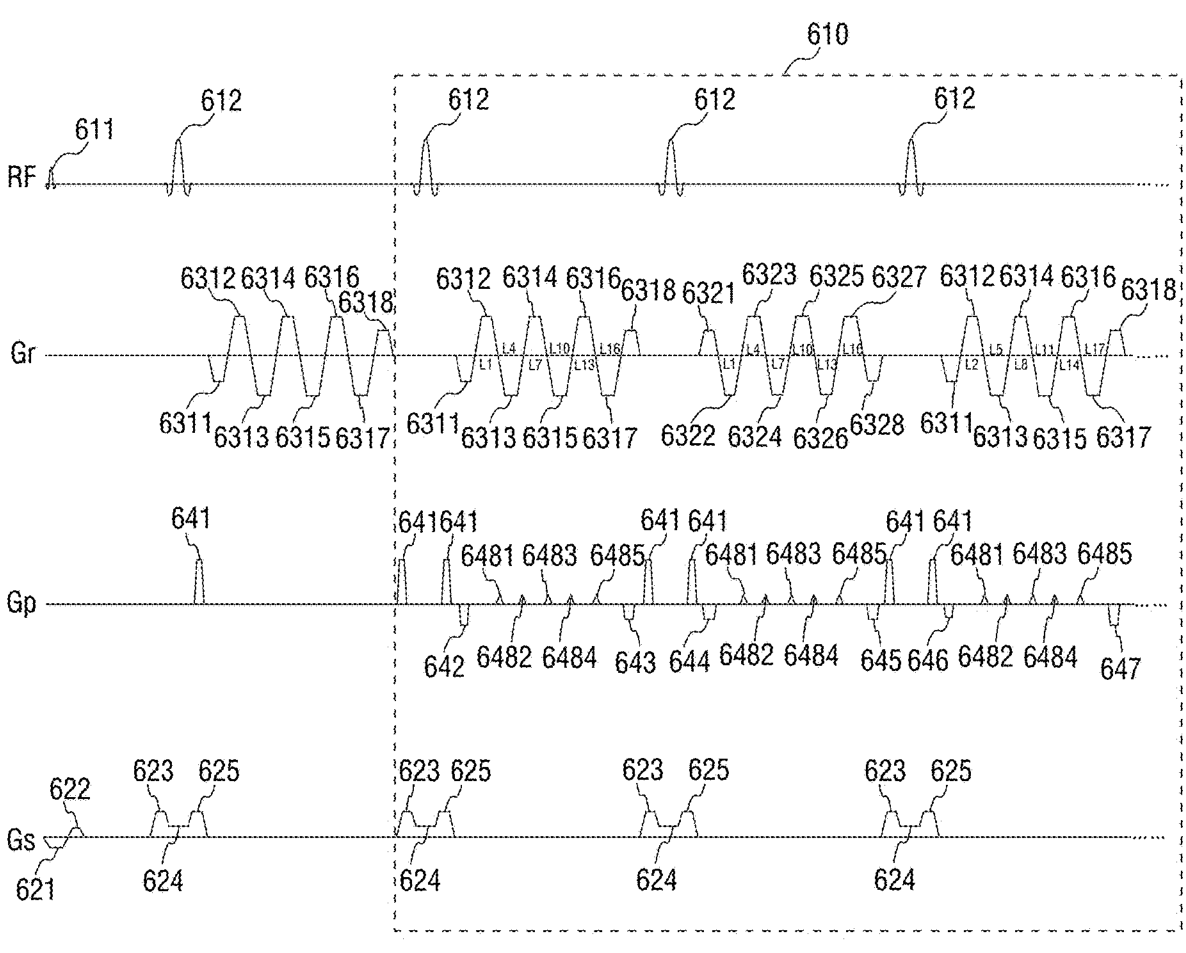
FIG. 6 is a schematic diagram of an EPI scanning process for collecting the ACS data in another application example of the present disclosure.

FIG. 6 is a schematic diagram of an EPI scanning process for collecting the ACS data in another application example of the present disclosure. The EPI scanning sequence may be the TGSE sequence, and in this example, the in-layer phase direction acceleration factor R is equal to 3, where RF represents the radio-frequency pulse transmitted to the target tissue, where 611 represents the 90° radio-frequency excited pulse, and 612 represents the first radio-frequency convergence pulse;

Gs represents a gradient field applied to the target tissue in the layer selection encoding direction, where 621 represents the first layer selection gradient pulse, 622 represents the convergence gradient pulse for the layer selection gradient, 623 and 625 represent the damage gradient pulse, and 624 represents the second layer selection gradient pulse;

Gr represents a gradient field applied to the target tissue in the readout direction, where 6311 and 6321 represent the pre-dispersed phase gradient pulse in the readout direction, 6312-6317 represent the first readout gradient pulse sequence, 6322-6327 represent the second readout gradient pulse sequence, and 6318 and 6328 represent the phase convergence gradient pulse in the readout direction; and Gp represents a gradient field applied to the target tissue in the phase encoding direction, where 641 represents the damage gradient pulse, 642, 644 and 646 represent the pre-dispersed phase gradient pulse in the phase encoding direction, 6481-6485 represent the first phase encoding gradient pulse sequence, and 643, 645 and 647 represent the phase convergence gradient pulse in the phase encoding direction.

As shown in FIG. 6, R is equal to 3, and therefore, the first radio-frequency convergence pulse 612 needs to be applied to a dotted box 610 for 6 times in total.

In one optional example, after simultaneously turning on the analog-digital converter to collect ACS data in a segmented manner, the step 504 further includes: re-sorting the ACS data collected in a segmented manner to obtain the ACS data in the k-space, where the re-sorting principle is that:

the corresponding line number of the ACS data collected by the lith positive readout gradient pulse in any odd-numbered segment 1 in the positive readout gradient k-space is 2R*(li−1)+ (l+1)/2, the corresponding line number of the ACS data collected by the ljth negative readout gradient pulse in any odd-numbered segment 1 in the negative readout gradient k-space is 2R*lj−R+ (l+1)/2, the corresponding line number of the ACS data collected by the rjth negative readout gradient pulse in any even-numbered segment r in the negative readout gradient k-space is 2R*(rj−1)+r/2, and the corresponding line number of the ACS data collected by the rith positive readout gradient pulse in any even-numbered segment r in the positive readout gradient k-space is 2R*ri−R+r/2, where 1≤l≤2R−1, 2≤r≤2R, li≥1, lj≥1, rj≥1 and ri≥1.

After the ACS data in the k-space are obtained, the data for correcting the phase error between the k-space lines in the step 503 can be used for correcting the phase error between the k-space lines (i.e., between the ACS data in different lines); then the ACS data with the corrected phase error are fit to obtain a DPG nucleus in a DPG reconstruction method; and when imaging data are collected in the EPI scanning process, the imaging data can be reconstructed by using the DPG nucleus to obtain a reconstructed image.

Figure 7:
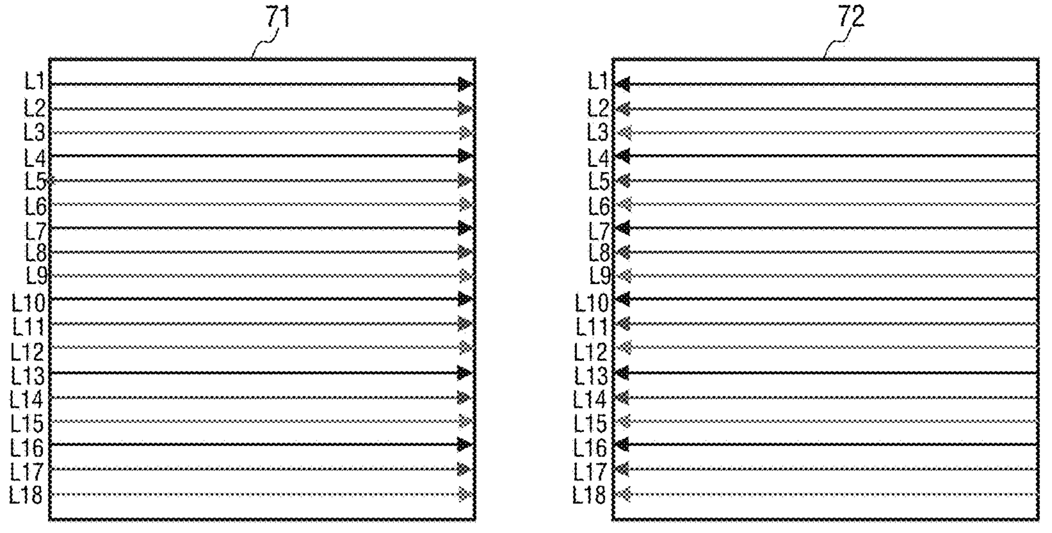
FIG. 7 is a representation diagram of a k-space after the ACS data collected in the EPI scanning process shown in FIG. 6 are re-sorted.

FIG. 7 is a representation diagram of a k-space after the ACS data collected in the EPI scanning process shown in FIG. 6 are re-sorted, where 71 represents the positive readout gradient k-space, and 72 represents the negative readout gradient k-space. As shown in FIG. 7, the corresponding relation between the ACS data of a first subframe of the segment l collected by the first spin echo in FIG. 6 and the line number of the k-space is as follows:

the ACS data collected by the 1st positive readout gradient pulse are located in the 1st line of the positive readout gradient k-space, i.e., L1 in 71;

the ACS data collected by the 1st negative readout gradient pulse are located in the 4th line of the negative readout gradient k-space, i.e., L4 in 72;

the ACS data collected by the 2nd positive readout gradient pulse are located in the 7th line of the positive readout gradient k-space, i.e., L7 in 71;

the ACS data collected by the 2nd negative readout gradient pulse are located in the 10th line of the negative readout gradient k-space, i.e., L10 in 72;

the ACS data collected by the 3rd positive readout gradient pulse are located in the 13th line of the positive readout gradient k-space, i.e., L13 in 71; and the ACS data collected by the 3rd negative readout gradient pulse are located in the 16th line of the negative readout gradient k-space, i.e., L16 in 72.

The corresponding relation between the ACS data of a second subframe of the segment 1 collected by the second spin echo and the line number of the k-space is as follows:

the ACS data collected by the 1st negative readout gradient pulse are located in the 1st line of the negative readout gradient k-space, i.e., L1 in 72;

the ACS data collected by the 1st positive readout gradient pulse are located in the 4th line of the positive readout gradient k-space, i.e., L4 in 71;

the ACS data collected by the 2nd negative readout gradient pulse are located in the 7th line of the negative readout gradient k-space, i.e., L7 in 72;

the ACS data collected by the 2nd positive readout gradient pulse are located in the 10th line of the positive readout gradient k-space, i.e., L10 in 71;

the ACS data collected by the 3rd negative readout gradient pulse are located in the 13th line of the negative readout gradient k-space, i.e., L13 in 72; and the ACS data collected by the 3rd positive readout gradient pulse are located in the 16th line of the positive readout gradient k-space, i.e., L16 in 71.

The corresponding relation between the ACS data of the first subframe of the segment 2 collected by the third spin echo and the line number of the k-space is as follows:

the ACS data collected by the 1st positive readout gradient pulse are located in the 2nd line of the positive readout gradient k-space, i.e., L2 in 71;

the ACS data collected by the 1st negative readout gradient pulse are located in the 5th line of the negative readout gradient k-space, i.e., L5 in 72;

the ACS data collected by the 2nd positive readout gradient pulse are located in the 8th line of the positive readout gradient k-space, i.e., L8 in 71;

the ACS data collected by the 2nd negative readout gradient pulse are located in the 11th line of the negative readout gradient k-space, i.e., L11 in 72;

the ACS data collected by the 3rd positive readout gradient pulse are located in the 14th line of the positive readout gradient k-space, i.e., L14 in 71; and the ACS data collected by the 3rd negative readout gradient pulse are located in the 17th line of the negative readout gradient k-space, i.e., L17 in 72.

The corresponding relation between the ACS data of the second subframe of the segment 2 collected by the fourth spin echo and the line number of the k-space is as follows:

the ACS data collected by the 1st negative readout gradient pulse are located in the 2nd line of the negative readout gradient k-space, i.e., L2 in 72;

the ACS data collected by the 1st positive readout gradient pulse are located in the 5th line of the positive readout gradient k-space, i.e., L5 in 71;

the ACS data collected by the 2nd negative readout gradient pulse are located in the 8th line of the negative readout gradient k-space, i.e., L8 in 72;

the ACS data collected by the 2nd positive readout gradient pulse are located in the 11th line of the positive readout gradient k-space, i.e., L11 in 71;

the ACS data collected by the 3rd negative readout gradient pulse are located in the 14th line of the negative readout gradient k-space, i.e., L14 in 72; and the ACS data collected by the 3rd positive readout gradient pulse are located in the 17th line of the positive readout gradient k-space, i.e., L17 in 71.

The rest may be deduced by analogy. The final representation of the k-space of the ACS data is shown in FIG. 7.

It is important to maintain roughly equal signal amplitude between the ACS data of the segments. Since the spin echoes generated at the beginning after one excitation have faster T2 attenuation, in order to reduce amplitude modulation between the ACS data of different segments, data collection may not be performed on a plurality of spin echoes generated at the beginning in practical application, specifically as follows:

in one optional example, after the radio-frequency excited pulse is applied and before the first radio-frequency convergence pulse is applied to the target tissue, the step 502 further includes: sequentially applying the first radio-frequency convergence pulse to the target tissue for preset times at intervals; applying the second layer selection gradient pulse to the target tissue in the layer selection encoding direction while the first radio-frequency convergence pulse is applied each time; and after the first radio-frequency convergence pulse is applied each time, applying the first readout gradient pulse sequence to the target tissue in the readout direction, forbidding the phase encoding gradients in the phase encoding direction, and simultaneously forbidding the analog-digital converter. The preset times may be 5 to 10 times.

FIG. 8 is a flow diagram of an EPI scanning method provided by yet another example of the present disclosure. The EPI scanning method includes the specific steps as follows:

step 801: in a single excited EPI scanning process, firstly, applying a 90° radio-frequency excited pulse to a target tissue, and simultaneously applying a first layer selection gradient pulse to the target tissue in a layer selection encoding direction;

step 802: after the radio-frequency excited pulse is applied, applying a first radio-frequency convergence pulse to the target tissue, and simultaneously applying a second layer selection gradient pulse to the target tissue in the layer selection encoding direction;

step 803: after the first radio-frequency convergence pulse is applied, applying a first readout gradient pulse sequence to the target tissue in a readout direction, forbidding phase encoding gradients in a phase encoding direction, and simultaneously turning on an analog-digital converter to collect data for correcting a phase error between k-space lines; and step 804: after the first readout gradient pulse sequence is applied, turning off the analog-digital converter, sequentially applying the first radio-frequency convergence pulse to the target tissue for 2R times at intervals, and applying the second layer selection gradient pulse to the target tissue in the layer selection encoding direction while the first radio-frequency convergence pulse is applied each time; after the first radio-frequency convergence pulse is applied each time, applying the first readout gradient pulse sequence to the target tissue in the readout direction, simultaneously applying a second phase encoding pulse sequence in the phase encoding direction, and simultaneously turning on the analog-digital converter to collect the auto calibration signal (ACS) data in a segmented manner, where R is the in-layer phase direction acceleration factor, and the first readout gradient pulse sequence is formed by a plurality of pairs of gradient pulses with opposite polarities; and when the first readout gradient pulse sequence applied to the target tissue in the readout direction is at the moment when the adjacent pairs of gradient pulses are alternate, applying a phase encoding pulse to the target tissue in the phase encoding direction.

The first readout gradient pulse sequence can be formed by a plurality of pairs of positive and negative gradient pulses or a plurality of pairs of negative and positive gradient pulses. The above example has the following beneficial technical effects:

I. The ACS data of all the segments are collected in one excitation, therefore, the sensibility of the ACS data of all the segments to movement is reduced, the phase error between the ACS data of all the segments is reduced, and the quality of the ACS data is improved, thereby reducing the influence of the movement on the final reconstructed image and reducing the Nyquist ghosting in the final reconstructed image.

II. The data for correcting the phase error between the k-space lines and the ACS data of all the segments are collected by using the same readout gradient pulse sequence, so that the deformation is consistent between the ACS data and the imaging data, thereby reducing the Nyquist ghosting in the final reconstructed image.

III. The ACS data of the segments are collected by a plurality of spin echoes generated in one excitation, so that the collected ACS data are not sensitive to the B0 unevenness. When high B0 unevenness occurs, the quality of the final reconstructed image is more stable, and the SNR of the reconstructed image is improved.

Figure 9:
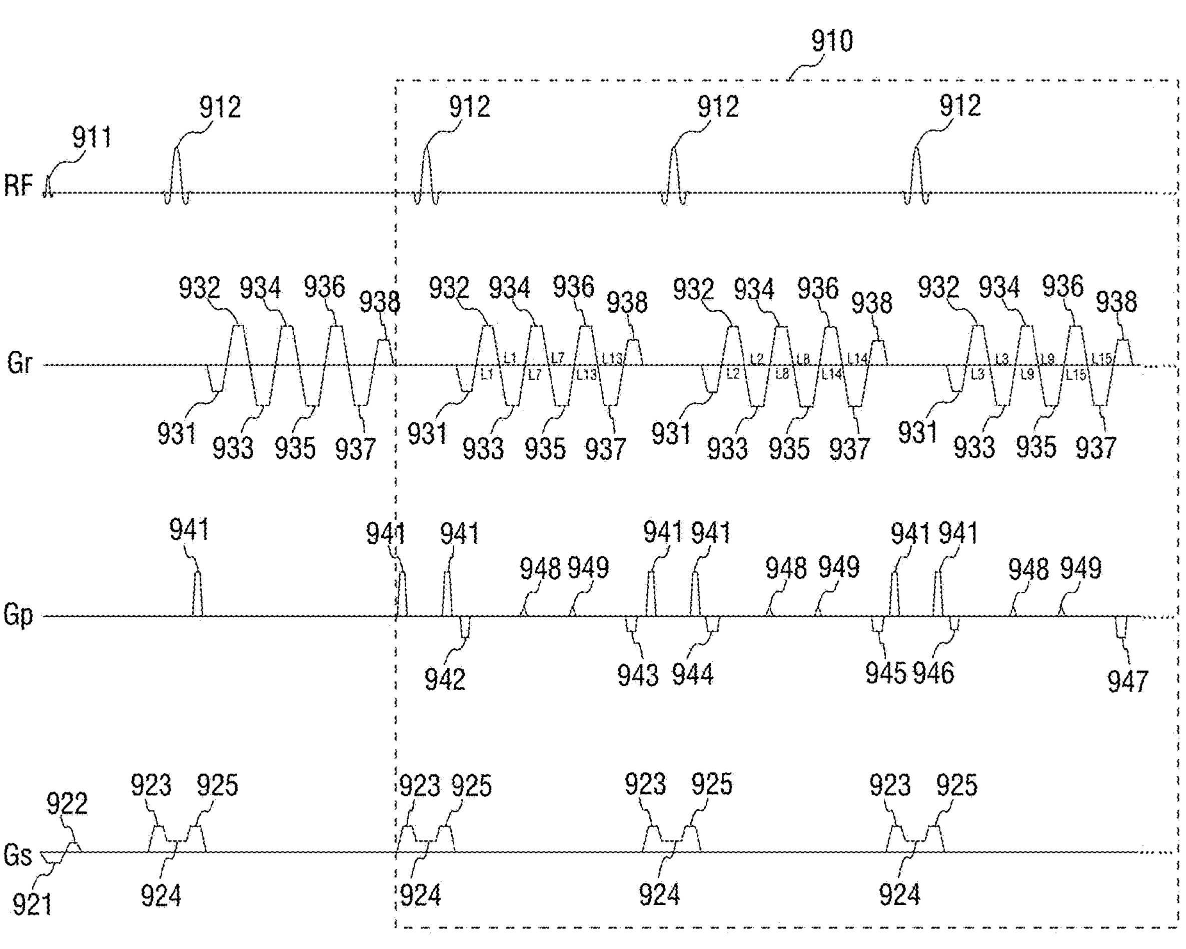
FIG. 9 is a schematic diagram of an EPI scanning process for collecting the ACS data in yet another application example of the present disclosure.

FIG. 9 is a schematic diagram of an EPI scanning process for collecting the ACS data in yet another application example of the present disclosure. The EPI scanning sequence may be the TGSE sequence, and in this example, the in-layer phase direction acceleration factor R is equal to 3, where RF represents the radio-frequency pulse transmitted to the target tissue, where 911 represents the 90° radio-frequency excited pulse, and 912 represents the first radio-frequency convergence pulse;

Gs represents a gradient field applied to the target tissue in the layer selection encoding direction, where 921 represents the first layer selection gradient pulse, 922 represents the convergence gradient pulse for the layer selection gradient, 923 and 925 represent the damage gradient pulse, and 924 represents the second layer selection gradient pulse;

Gr represents a gradient field applied to the target tissue in the readout direction, where 931 represents the pre-dispersed phase gradient pulse in the readout direction, 932-937 represents the first readout gradient pulse sequence, and 938 represents the phase convergence gradient pulse in the readout direction; and Gp represents a gradient field applied to the target tissue in the phase encoding direction, where 941 represents the damage gradient pulse, 942, 944 and 946 represent the pre-dispersed phase gradient pulse in the phase encoding direction, 948-949 represent the second phase encoding gradient pulse sequence, and 943, 945 and 947 represent the phase convergence gradient pulse in the phase encoding direction.

As shown in FIG. 9, R is equal to 3, and therefore, the first radio-frequency convergence pulse 912 needs to be applied to a dotted box 910 for 6 times in total.

In one optional example, after simultaneously turning on the analog-digital converter to collect ACS data in a segmented manner, the step 804 further includes: re-sorting the ACS data collected in a segmented manner to obtain the ACS data in the k-space, where the re-sorting principle is that:

the corresponding line number of the ACS data collected by the tith positive readout gradient pulse in any segment t in the positive readout gradient k-space is $2R*(ti-1)+t$, and the corresponding line number of the ACS data collected by the tjth negative readout gradient pulse in any segment 1 in the negative readout gradient k-space is $2R*(tj-1)+t$, where $1 \le t \le R$, $ti \ge 1$ and $tj \ge 1$.

After the ACS data in the k-space are obtained, the data for correcting the phase error between the k-space lines in the step 803 can be used for correcting the phase error between the k-space lines (i.e., between the ACS data in different lines); then the ACS data with the corrected phase error are fit to obtain a DPG nucleus in a DPG reconstruction method; and when imaging data are collected in the EPI scanning process, the imaging data can be reconstructed by using the DPG nucleus to obtain a reconstructed image.

Figure 10:
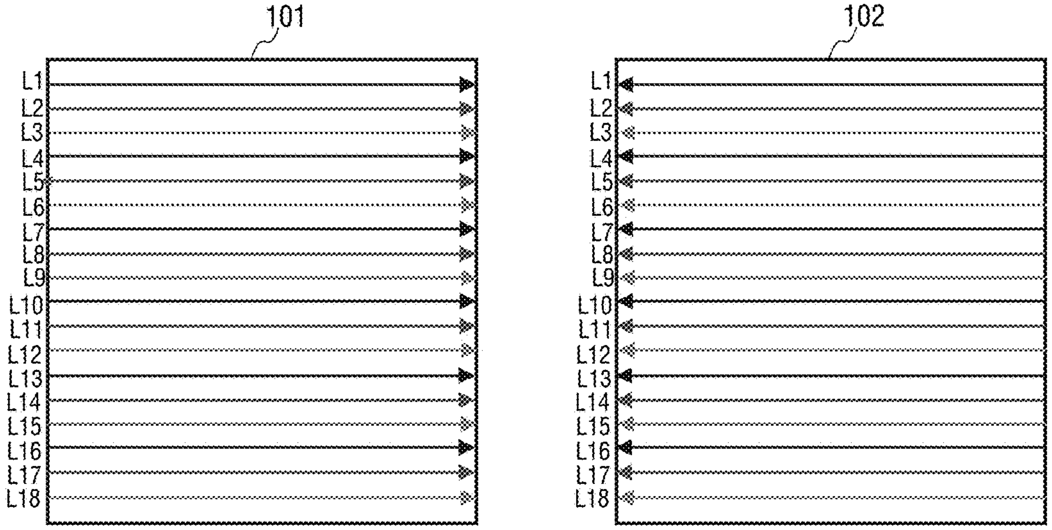
FIG. 10 is a representation diagram of a k-space after the ACS data collected in the EPI scanning process shown in FIG. 9 are re-sorted.

FIG. 10 is a representation diagram of a k-space after the ACS data collected in the EPI scanning process shown in FIG. 9 are re-sorted, where 101 represents the positive readout gradient k-space, and 102 represents the negative readout gradient k-space. As shown in FIG. 10, the corresponding relation between the ACS data of two subframes of the segment 1 collected by the first spin echo in FIG. 9 and the line number of the k-space is as follows:

- the ACS data collected by the 1st positive readout gradient pulse are located in the 1st line of the positive readout gradient k-space, i.e., L1 in 101;
- the ACS data collected by the 1st negative readout gradient pulse are located in the 1st line of the negative readout gradient k-space, i.e., L1 in 102;
- the ACS data collected by the 2nd positive readout gradient pulse are located in the 7th line of the positive readout gradient k-space, i.e., L7 in 101;
- the ACS data collected by the 2nd negative readout gradient pulse are located in the 7th line of the negative readout gradient k-space, i.e., L7 in 102;
- the ACS data collected by the 3rd positive readout gradient pulse are located in the 13th line of the positive readout gradient k-space, i.e., L13 in 101; and
- the ACS data collected by the 3rd negative readout gradient pulse are located in the 13th line of the negative readout gradient k-space, i.e., L13 in 102.

The corresponding relation between the ACS data of two subframes of the segment 2 collected by the second spin echo and the line number of the k-space is as follows:

- the ACS data collected by the 1st positive readout gradient pulse are located in the 2nd line of the positive readout gradient k-space, i.e., L2 in 101;
- the ACS data collected by the 1st negative readout gradient pulse are located in the 2nd line of the negative readout gradient k-space, i.e., L2 in 102;
- the ACS data collected by the 2nd positive readout gradient pulse are located in the 8th line of the positive readout gradient k-space, i.e., L8 in 71;
- the ACS data collected by the 2nd negative readout gradient pulse are located in the 8th line of the negative readout gradient k-space, i.e., L8 in 72;
- the ACS data collected by the 3rd positive readout gradient pulse are located in the 14th line of the positive readout gradient k-space, i.e., L14 in 71; and
- the ACS data collected by the 3rd negative readout gradient pulse are located in the 14th line of the negative readout gradient k-space, i.e., L14 in 72.

The corresponding relation between the ACS data of two subframes of the segment 3 collected by the third spin echo and the line number of the k-space is as follows:

- the ACS data collected by the 1st positive readout gradient pulse are located in the 3rd line of the positive readout gradient k-space, i.e., L3 in 101;
- the ACS data collected by the 1st negative readout gradient pulse are located in the 3rd line of the negative readout gradient k-space, i.e., L3 in 102;
- the ACS data collected by the 2nd positive readout gradient pulse are located in the 9th line of the positive readout gradient k-space, i.e., L9 in 101;
- the ACS data collected by the 2nd negative readout gradient pulse are located in the 9th line of the negative readout gradient k-space, i.e., L9 in 102;
- the ACS data collected by the 3rd positive readout gradient pulse are located in the 15th line of the positive readout gradient k-space, i.e., L15 in 101; and
- the ACS data collected by the 3rd negative readout gradient pulse are located in the 15th line of the negative readout gradient k-space, i.e., L15 in 102.

The corresponding relation between the ACS data of two subframes of the segment 4 collected by the fourth spin echo and the line number of the k-space is as follows:

- the ACS data collected by the 1st positive readout gradient pulse are located in the 4th line of the positive readout gradient k-space, i.e., L4 in 101;
- the ACS data collected by the 1st negative readout gradient pulse are located in the 4th line of the negative readout gradient k-space, i.e., L4 in 102;
- the ACS data collected by the 2nd positive readout gradient pulse are located in the 10th line of the positive readout gradient k-space, i.e., L10 in 101;
- the ACS data collected by the 2nd negative readout gradient pulse are located in the 10th line of the negative readout gradient k-space, i.e., L10 in 102;
- the ACS data collected by the 3rd positive readout gradient pulse are located in the 16th line of the positive readout gradient k-space, i.e., L16 in 101; and
- the ACS data collected by the 3rd negative readout gradient pulse are located in the 16th line of the negative readout gradient k-space, i.e., L16 in 102.

The rest may be deduced by analogy. The final representation of the k-space of all the ACS data is shown in FIG. 10.

It is important to maintain roughly equal signal amplitude between the ACS data of the segments. Since the spin echoes generated at the beginning after one excitation have faster T2 attenuation, in order to reduce amplitude modulation between the ACS data of different segments, data collection may not be performed on a plurality of spin echoes generated at the beginning in practical application, specifically as follows:

- in one optional example, after the radio-frequency excited pulse is applied and before the first radio-frequency convergence pulse is applied to the target tissue, the step 802 further includes: sequentially applying the first radio-frequency convergence pulse to the target tissue for preset times at intervals; applying the second layer selection gradient pulse to the target tissue in the layer selection encoding direction while the first radio-frequency convergence pulse is applied each time; and after the first radio-frequency convergence pulse is applied each time, applying the first readout gradient pulse sequence to the target tissue in the readout direction, forbidding the phase encoding gradients in the phase encoding direction, and simultaneously forbidding the analog-digital converter. The preset times may be 5 to 10 times.

Figure 11:
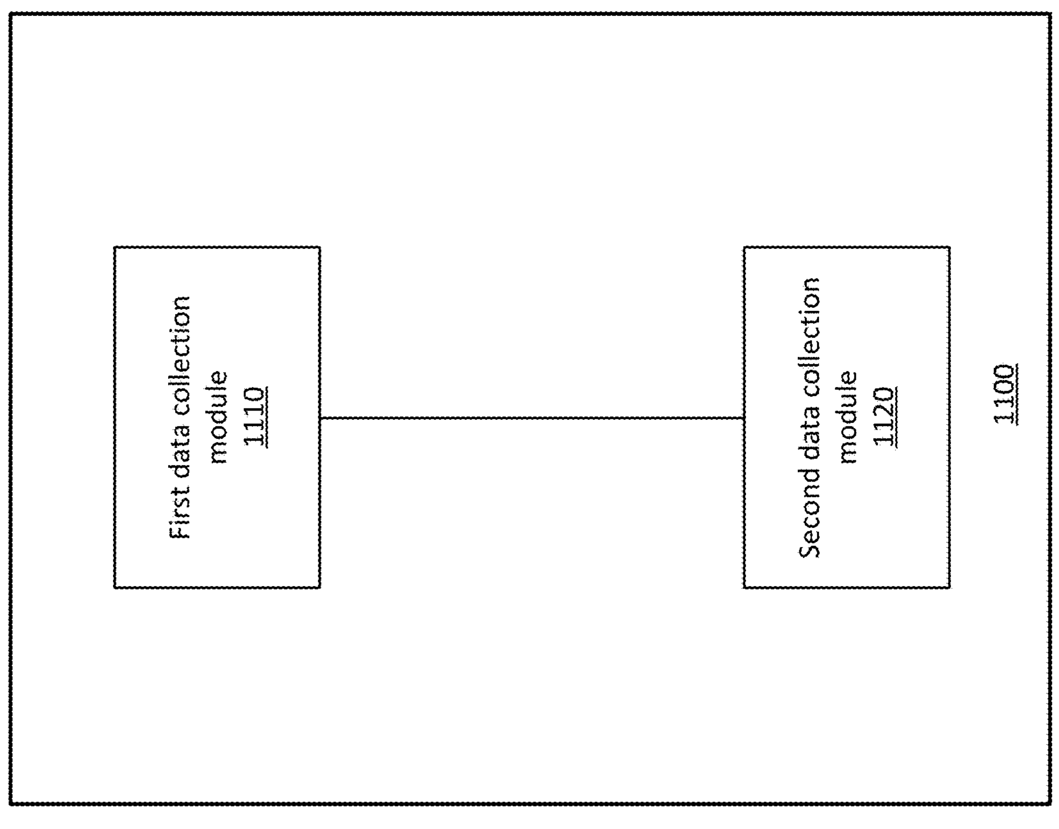
FIG. 11 is a schematic structure diagram of an EPI scanning device provided by one example of the present disclosure.

FIG. 11 is a schematic structure diagram of an EPI scanning device 1100 provided by one example of the present disclosure. The device 1100 mainly includes: a first data collection module 1110 and a second data collection module 1120, where

- the first data collection module 1110 is used for in the single excited EPI scanning process, firstly, applying the 90° radio-frequency excited pulse to the target tissue, and simultaneously applying the first layer selection gradient pulse to the target tissue in the layer selection encoding direction; after the radio-frequency excited pulse is applied, applying the first radio-frequency convergence pulse to the target tissue, and simultaneously applying the second layer selection gradient pulse to the target tissue in the layer selection encoding direction; and after the first radio-frequency convergence pulse is applied, applying the first readout gradient pulse sequence to the target tissue in the readout direction, forbidding the phase encoding gradients in the phase encoding direction, and simultaneously turning on the analog-digital converter to collect the data for correcting the phase error between the k-space lines; and the second data collection module 1120 is used for after the first readout gradient pulse sequence is applied, turning off the analog-digital converter, sequentially applying the first radio-frequency convergence pulse to the target tissue for R times at intervals, and applying the second layer selection gradient pulse to the target tissue in the layer selection encoding direction while the first radio-frequency convergence pulse is applied each time; after the first radio-frequency convergence pulse is applied each time, applying the first readout gradient pulse sequence to the target tissue in the readout direction, simultaneously applying the first phase encoding pulse sequence in the phase encoding direction, and simultaneously turning on the analog-digital converter to collect the auto calibration signal (ACS) data in a segmented manner, where R is the in-layer phase direction acceleration factor, and the first readout gradient pulse sequence is formed by a plurality of pairs of gradient pulses with opposite polarities; and when the first readout gradient pulse sequence applied to the target tissue in the readout direction is at the moment when the polarity of the gradient pulse changes, applying a phase encoding pulse to the target tissue in the phase encoding direction.

In one optional example, after simultaneously turning on the analog-digital converter to collect ACS data in a segmented manner, the second data collection module 1120 is further used for re-sorting the ACS data collected in a segmented manner to obtain the ACS data in the k-space, where the re-sorting principle is that: the corresponding line number of the collected ACS data in the pith line in any segment p in the k-space after re-sorting is $R*(pi-1)+p$, where $1 \le p \le R$ and $pi \ge 1$.

In one optional example, after the radio-frequency excited pulse is applied and before the first radio-frequency convergence pulse is applied to the target tissue, the first data collection module 1110 is further used for sequentially applying the first radio-frequency convergence pulse to the target tissue for preset times at intervals; applying the second layer selection gradient pulse to the target tissue in the layer selection encoding direction while the first radio-frequency convergence pulse is applied each time; and after the first radio-frequency convergence pulse is applied each time, applying the first readout gradient pulse sequence to the target tissue in the readout direction, forbidding the phase encoding gradients in the phase encoding direction, and simultaneously forbidding the analog-digital converter.

Figure 12:
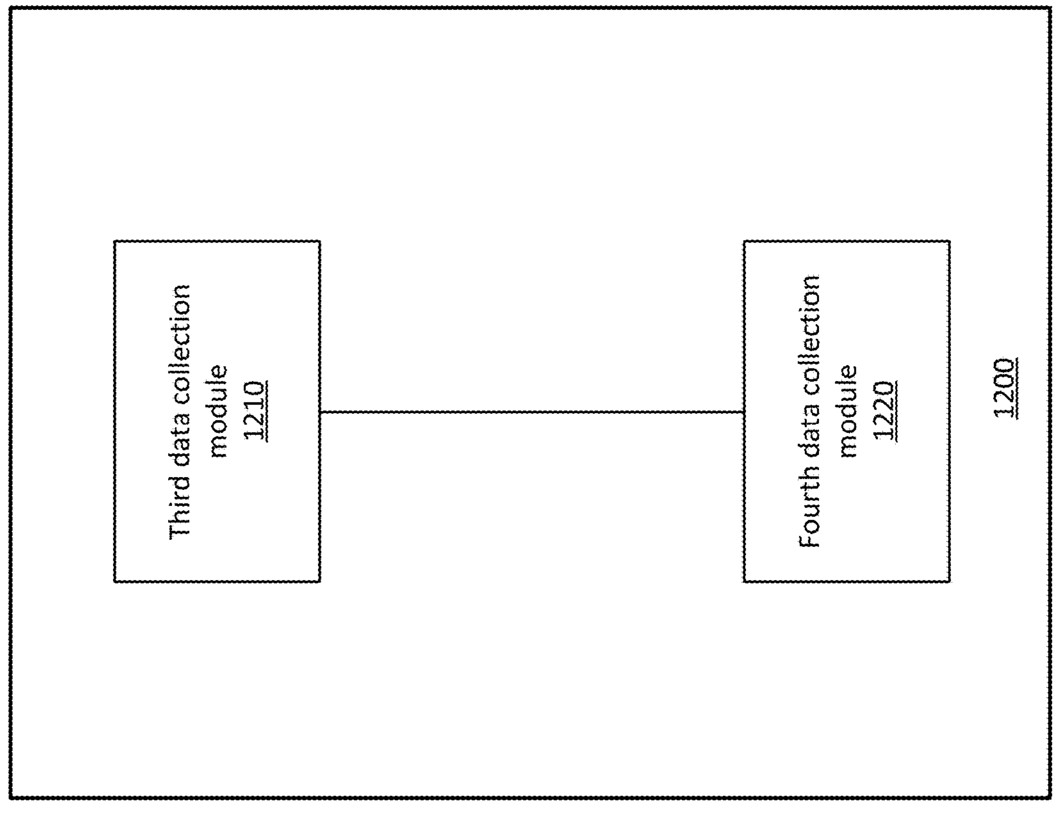
FIG. 12 is a schematic structure diagram of an EPI scanning device provided by another example of the present disclosure.

FIG. 12 is a schematic structure diagram of an EPI scanning device 1200 provided by another example of the present disclosure. The device 1200 mainly includes: a third data collection module 1210 and a fourth data collection module 1220, where the third data collection module 1210 is used for in the single excited EPI scanning process, firstly, applying the 90° radio-frequency excited pulse to the target tissue, and simultaneously applying the first layer selection gradient pulse to the target tissue in the layer selection encoding direction; after the radio-frequency excited pulse is applied, applying the first radio-frequency convergence pulse to the target tissue, and simultaneously applying the second layer selection gradient pulse to the target tissue in the layer selection encoding direction; and after the first radio-frequency convergence pulse is applied, applying the first readout gradient pulse sequence to the target tissue in the readout direction, forbidding the phase encoding gradients in the phase encoding direction, and simultaneously turning on the analog-digital converter to collect the data for correcting the phase error between the k-space lines; and the fourth data collection module 1220 is used for after the first readout gradient pulse sequence is applied, turning off the analog-digital converter, sequentially applying the first radio-frequency convergence pulse to the target tissue for 2R times at intervals, and applying the second layer selection gradient pulse to the target tissue in the layer selection encoding direction while the first radio-frequency convergence pulse is applied each time; after the first radio-frequency convergence pulse is applied each time, applying the first or second readout gradient pulse sequence to the target tissue in the readout direction, simultaneously applying the first phase encoding pulse sequence in the phase encoding direction, and simultaneously turning on the analog-digital converter to collect the auto calibration signal (ACS) data in a segmented manner, where R is the in-layer phase direction acceleration factor, the first readout gradient pulse sequence is applied to the target tissue at odd-numbered times in the 2R times, the second readout gradient pulse sequence is applied to the target tissue at even-numbered times in the 2R times, each of the first and second readout gradient pulse sequence is formed by a plurality of pairs of gradient pulses with opposite polarities, and the polarity of the first readout gradient pulse sequence is opposite to that of the second readout gradient pulse sequence; and when the first or second readout gradient pulse sequence applied to the target tissue in the readout direction is at the moment when the polarity of the gradient pulse changes, applying a phase encoding pulse to the target tissue in the phase encoding direction.

In one optional example, after simultaneously turning on the analog-digital converter to collect ACS data in a segmented manner, the fourth data collection module 1220 is further used for re-sorting the ACS data collected in a segmented manner to obtain the ACS data in the positive readout gradient k-space and the ACS data in the negative readout gradient k-space, where the re-sorting principle is that:

the corresponding line number of the ACS data collected by the lith positive readout gradient pulse in any odd-numbered segment l in the positive readout gradient k-space is $2R*(li-1)+(l+1)/2$, the corresponding line number of the ACS data collected by the ljth negative readout gradient pulse in any odd-numbered segment l in the negative readout gradient k-space is $2R*lj-R+(l+1)/2$, the corresponding line number of the ACS data collected by the rjth negative readout gradient pulse in any even-numbered segment r in the negative readout gradient k-space is $2R*(rj-1)+r/2$, and the corresponding line number of the ACS data collected by the rith positive readout gradient pulse in any even-numbered segment r in the positive readout gradient k-space is $2R*ri-R+r/2$, where $l \le l \le 2R-1$, $2 \le r \le 2R$, $li \ge 1$, $lj \ge 1$, $rj \ge 1$ and $ri \ge 1$.

In one optional example, after the radio-frequency excited pulse is applied and before the first radio-frequency convergence pulse is applied to the target tissue, the third data collection module 1210 is further used for sequentially applying the first radio-frequency convergence pulse to the target tissue for preset times at intervals; applying the second layer selection gradient pulse to the target tissue in the layer selection encoding direction while the first radio-frequency convergence pulse is applied each time; and after the first radio-frequency convergence pulse is applied each time, applying the first readout gradient pulse sequence to the target tissue in the readout direction, forbidding the phase encoding gradients in the phase encoding direction, and simultaneously forbidding the analog-digital converter.

Figure 13:
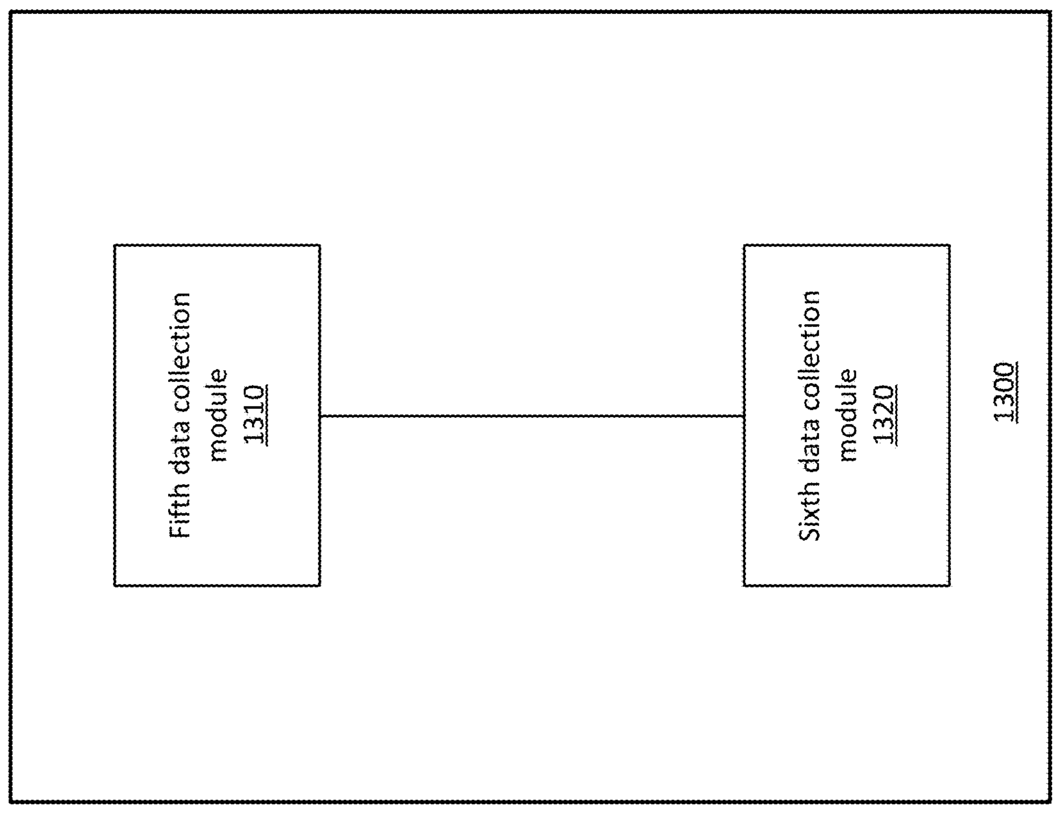
FIG. 13 is a schematic structure diagram of an EPI scanning device provided by yet another example of the present disclosure.

FIG. 13 is a schematic structure diagram of an EPI scanning device 1300 provided by yet another example of the present disclosure. The device 1300 mainly includes: a fifth data collection module 1310 and a sixth data collection module 1320, where the fifth data collection module 1310 is used for in the single excited EPI scanning process, firstly, applying the 90° radio-frequency excited pulse to the target tissue, and simultaneously applying the first layer selection gradient pulse to the target tissue in the layer selection encoding direction; after the radio-frequency excited pulse is applied, applying the first radio-frequency convergence pulse to the target tissue, and simultaneously applying the second layer selection gradient pulse to the target tissue in the layer selection encoding direction; and after the first radio-frequency convergence pulse is applied, applying the first readout gradient pulse sequence to the target tissue in the readout direction, forbidding the phase encoding gradients in the phase encoding direction, and simultaneously turning on the analog-digital converter to collect the data for correcting the phase error between the k-space lines; and the sixth data collection module 1320 is used for after the first readout gradient pulse sequence is applied, turning off the analog-digital converter, sequentially applying the first radio-frequency convergence pulse to the target tissue for 2R times at intervals, and applying the second layer selection gradient pulse to the target tissue in the layer selection encoding direction while the first radio-frequency convergence pulse is applied each time; after the first radio-frequency convergence pulse is applied each time, applying the first readout gradient pulse sequence to the target tissue in the readout direction, simultaneously applying a second phase encoding pulse sequence in the phase encoding direction, and simultaneously turning on the analog-digital converter to collect the auto calibration signal (ACS) data in a segmented manner, where R is the in-layer phase direction acceleration factor, and the first readout gradient pulse sequence is formed by a plurality of pairs of gradient pulses with opposite polarities; and when the first readout gradient pulse sequence applied to the target tissue in the readout direction is at the moment when the adjacent pairs of gradient pulses are alternate, applying a phase encoding pulse to the target tissue in the phase encoding direction.

In one optional example, after simultaneously turning on the analog-digital converter to collect ACS data in a segmented manner, the sixth data collection module 1320 is further used for re-sorting the ACS data collected in a segmented manner to obtain the ACS data in the k-space, where the re-sorting principle is that:

the corresponding line number of the ACS data collected by the tith positive readout gradient pulse in any segment t in the positive readout gradient k-space is 2R*(ti−1)+t, and the corresponding line number of the ACS data collected by the tjth negative readout gradient pulse in any segment 1 in the negative readout gradient k-space is 2R*(tj−1)+t, where 1≤t≤2R, ti≥1 and tj≥1.

In one optional example, after the radio-frequency excited pulse is applied and before the first radio-frequency convergence pulse is applied to the target tissue, the fifth data collection module 1310 is further used for sequentially applying the first radio-frequency convergence pulse to the target tissue for preset times at intervals; applying the second layer selection gradient pulse to the target tissue in the layer selection encoding direction while the first radio-frequency convergence pulse is applied each time; and after the first radio-frequency convergence pulse is applied each time, applying the first readout gradient pulse sequence to the target tissue in the readout direction, forbidding the phase encoding gradients in the phase encoding direction, and simultaneously forbidding the analog-digital converter.

The example of the present disclosure further provides an MRI system. The MRI system includes the EPI scanning device according to any one of the above examples.

It is understood by a person skilled in the art that the features set forth in all the examples and/or claims of the present disclosure can be combined and/or integrated in multiple ways, even if such combination and/or integration are not explicitly stated in the present application. Especially, the features set forth in all the examples and/or claims of the present disclosure can be combined and/or integrated in multiple ways without deviating from the spirit and teachings of the present application, and all the combinations and/or integrations shall fall within the scope disclosed in the present application.

The principle and implementation of the present application are described with reference to specific examples herein, and the above examples are only used for assisting in understanding the method and core thought of the present application, and are not intended to limit the present application. Modifications to the detailed description and the application scope can be made by a person skilled in the art according to the thought, spirit and principle of the present application, and any amendment, equivalent replacement, improvement and the like shall fall within the protection scope of the present application.

The various components described herein may be referred to as "modules." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such modules, as applicable and relevant, may alternatively be referred to herein as "circuitry," "controllers," "processors," or "processing circuitry," or alternatively as noted herein.

What is claimed is:

1. An echo planar imaging (EPI) scanning method, comprising:

in a single excited EPI scanning process, simultaneously applying a 90° radio-frequency (RF) excited pulse to a target tissue with a first layer selection gradient pulse in a layer selection encoding direction;

after applying the RF excited pulse, simultaneously applying a first RF convergence pulse to the target tissue with a second layer selection gradient pulse in the layer selection encoding direction;

after applying the first RF convergence pulse, simultaneously (i) applying a first readout gradient pulse sequence to the target tissue in a readout direction and (ii) turning on an analog-digital converter (ADC) to collect data for correcting a phase error between k-space lines while forbidding phase encoding gradients in a phase encoding direction; and after applying the first readout gradient pulse sequence, turning off the ADC, sequentially applying the first RF convergence pulse to the target tissue for R times at intervals, and applying the second layer selection gradient pulse to the target tissue in the layer selection encoding direction while the first RF convergence pulse is applied each time;

after applying the first RF convergence pulse each time, simultaneously (i) applying the first readout gradient pulse sequence to the target tissue in the readout direction, (ii) applying a first phase encoding pulse sequence in the phase encoding direction, and (iii) turning on the ADC to collect auto calibration signal (ACS) data in a segmented manner, wherein R represents an in-layer phase direction acceleration factor, and wherein the first readout gradient pulse sequence is formed by a plurality of pairs of gradient pulses with opposite polarities, and when the first readout gradient pulse sequence applied to the target tissue in the readout direction is when the polarity of the gradient pulse changes, applying a phase encoding pulse to the target tissue in the phase encoding direction.

2. The method according to claim 1, further comprising:

after simultaneously turning on the ADC to collect ACS data in a segmented manner, re-sorting the ACS data collected in a segmented manner to obtain ACS data in k-space, wherein the re-sorting is performed such that a corresponding line number of the ACS data collected by the p-ith readout gradient pulse in any segment p in k-space satisfies $R*(pi-1)+p$, wherein $1 \le p \le R$ and $pi \ge 1$.

3. The method according to claim 1, further comprising:

after the RF excited pulse is applied to the target tissue and before the first RF convergence pulse is applied to the target tissue:

sequentially applying the first RF convergence pulse to the target tissue for preset times at intervals;

applying the second layer selection gradient pulse to the target tissue in the layer selection encoding direction while the first RF convergence pulse is applied each time; and after the first RF convergence pulse is applied each time, applying the first readout gradient pulse sequence to the target tissue in the readout direction, and simultaneously (i) forbidding the phase encoding gradients in the phase encoding direction, and (ii) turning off the ADC.

4. An echo planar imaging (EPI) scanning method, comprising:

in a single excited EPI scanning process, simultaneously applying a 90° radio-frequency (RF) excited pulse and a first layer selection gradient pulse to a target tissue in a layer selection encoding direction;

after applying the RF excited pulse, simultaneously applying a first RF convergence pulse and a second layer selection gradient pulse to the target tissue in the layer selection encoding direction;

after applying the first RF convergence pulse, simultaneously (i) applying a first readout gradient pulse sequence to the target tissue in a readout direction, and (ii) turning on an analog-digital converter (ADC) to collect data for correcting a phase error between k-space lines while forbidding phase encoding gradients in a phase encoding direction; and after applying the first readout gradient pulse sequence, turning off the ADC, and sequentially applying the first RF convergence pulse to the target tissue for 2R times at intervals, and applying the second layer selection gradient pulse to the target tissue in the layer selection encoding direction while the first RF convergence pulse is applied each time;

after the first RF convergence pulse is applied each time, applying the first or second readout gradient pulse sequence to the target tissue in the readout direction, and simultaneously (i) applying a first phase encoding pulse sequence in the phase encoding direction, and (ii) turning on the analog-digital converter to collect auto calibration signal (ACS) data in a segmented manner, wherein R represents an in-layer phase direction acceleration factor, wherein the first readout gradient pulse sequence is applied to the target tissue at odd-numbered times in the 2R times, wherein the second readout gradient pulse sequence is applied to the target tissue at even-numbered times in the 2R times, each of the first and second readout gradient pulse sequence being formed by a plurality of pairs of gradient pulses with opposite polarities, and the polarity of the first readout gradient pulse sequence being opposite to that of the second readout gradient pulse sequence; and when the first or second readout gradient pulse sequence applied to the target tissue in the readout direction is when the polarity of the gradient pulse changes, applying a phase encoding pulse to the target tissue in the phase encoding direction.

5. The method according to claim 4, further comprising:

after simultaneously turning on the ADC to collect ACS data in a segmented manner:

re-sorting the ACS data collected in a segmented manner to obtain ACS data in a positive readout gradient k-space and ACS data in a negative readout gradient k-space, wherein the re-sorting is performed such that:

a corresponding line number of the ACS data collected by the l-ith positive readout gradient pulse in any odd-numbered segment 1 in the positive readout gradient k-space is $2R*(li-1)+(l+1)/2$, a corresponding line number of the ACS data collected by the l-jth negative readout gradient pulse in any odd-numbered segment 1 in the negative readout gradient k-space is $2R*lj-R+(l+1)/2$, a corresponding line number of the ACS data collected by the r-jth negative readout gradient pulse in any even-numbered segment r in the negative readout gradient k-space is $2R*(rj-1)+r/2$, and a corresponding line number of the ACS data collected by the r-ith positive readout gradient pulse in any even-numbered segment r in the positive readout gradient k-space is $2R*ri-R+r/2$, and wherein $1 \le l \le 2R-1$, $2 \le r \le 2R$, $li \ge 1$, $lj \ge 1$, $rj \ge 1$, and $ri \ge 1$.

6. The method according to claim 4, further comprising: after applying the RF excited pulse and before applying the first RF convergence pulse to the target tissue:

sequentially applying the first RF convergence pulse to the target tissue for preset times at intervals;

applying the second layer selection gradient pulse to the target tissue in the layer selection encoding direction while the first radio-frequency convergence pulse is applied each time; and after the first RF convergence pulse is applied each time, applying the first readout gradient pulse sequence to the target tissue in the readout direction, and simultaneously (i) forbidding the phase encoding gradients in the phase encoding direction, and (ii) turning off the ADC.

7. An echo planar imaging (EPI) scanning method, comprising:

in a single excited EPI scanning process, simultaneously applying a 90° radio-frequency (RF) excited pulse and a first layer selection gradient pulse to a target tissue in a layer selection encoding direction;

after applying the RF excited pulse, simultaneously applying a first RF convergence pulse and a second layer selection gradient pulse to the target tissue in the layer selection encoding direction;

after applying the first RF convergence pulse, simultaneously (i) applying a first readout gradient pulse sequence to the target tissue in a readout direction, and (ii) turning on an analog-digital converter (ADC) to collect data for correcting a phase error between k-space lines while forbidding phase encoding gradients in a phase encoding direction; and after applying the first readout gradient pulse sequence, turning off the ADC, sequentially applying the first RF convergence pulse to the target tissue for 2R times at intervals, and applying the second layer selection gradient pulse to the target tissue in the layer selection encoding direction while the first RF convergence pulse is applied each time;

after the first RF convergence pulse is applied each time, applying the first readout gradient pulse sequence to the target tissue in the readout direction, and simultaneously (i) applying a second phase encoding pulse sequence in the phase encoding direction, and (ii) turning on the ADC to collect auto calibration signal (ACS) data in a segmented manner, wherein R represents an in-layer phase direction acceleration factor, and the first readout gradient pulse sequence is formed by a plurality of pairs of gradient pulses with opposite polarities; and when the first readout gradient pulse sequence applied to the target tissue in the readout direction is when adjacent pairs of gradient pulses are alternate, applying one phase encoding pulse to the target tissue in the phase encoding direction.

8. The method according to claim 7, further comprising: after simultaneously turning on the ADC to collect ACS data in a segmented manner:

re-sorting the ACS data collected in a segmented manner to obtain ACS data in the k-space, wherein the re-sorting is performed such that:

a corresponding line number of the ACS data collected by the t-ith positive readout gradient pulse in any segment t in a positive readout gradient k-space is 2R*(ti−1)+t, and a corresponding line number of the ACS data collected by the t-jth negative readout gradient pulse in any segment 1 in a negative readout gradient k-space is 2R*(tj−1)+t, wherein 1≤t≤2R, ti≥1, and tj≥1.

9. The method according to claim 7, further comprising: after the RF excited pulse is applied and before the first RF convergence pulse is applied to the target tissue:

sequentially applying the first RF convergence pulse to the target tissue for preset times at intervals;

applying the second layer selection gradient pulse to the target tissue in the layer selection encoding direction while the first radio-frequency convergence pulse is applied each time; and after the first RF convergence pulse is applied each time, applying the first readout gradient pulse sequence to the target tissue in the readout direction, and simultaneously (i) forbidding the phase encoding gradients in the phase encoding direction, and (ii) turning off the ADC.

10. An echo planar imaging (EPI) scanning device, comprising:

first data collection circuitry configured to cause the EPI scanning device to perform a single excited EPI scanning process by:

simultaneously applying a 90° radio-frequency (RF) excited pulse and a first layer selection gradient pulse to a target tissue in a layer selection encoding direction;

after applying the RF excited pulse, simultaneously applying a first RF convergence pulse and a second layer selection gradient pulse to the target tissue in the layer selection encoding direction; and after applying the first RF convergence pulse, simultaneously (i) applying a first readout gradient pulse sequence to the target tissue in a readout direction, and (ii) turning on an analog-digital converter (ADC) to collect data for correcting a phase error between k-space lines while forbidding phase encoding gradients in a phase encoding direction; and second data collection circuitry configured to cause the EPI scanning device to:

after applying the first readout gradient pulse sequence, turn off the ADC, sequentially apply the first RF convergence pulse to the target tissue for R times at intervals, and apply the second layer selection gradient pulse to the target tissue in the layer selection encoding direction while the first RF convergence pulse is applied each time;

after applying the first RF convergence pulse each time, simultaneously (i) apply the first readout gradient pulse sequence to the target tissue in the readout direction, (ii) apply a first phase encoding pulse sequence in the phase encoding direction, and (iii) turn on the ADC to collect auto calibration signal (ACS) data in a segmented manner, wherein R is an in-layer phase direction acceleration factor, and wherein the first readout gradient pulse sequence is formed by a plurality of pairs of gradient pulses with opposite polarities, and when the first readout gradient pulse sequence applied to the target tissue in the readout direction is when the polarity of the gradient pulse changes, apply a phase encoding pulse to the target tissue in the phase encoding direction.

11. The EPI scanning device according to claim 10, wherein the second data collection circuitry is further configured to cause the EPI scanning device to, after simultaneously turning on the ADC to collect ACS data in a segmented manner:

re-sort the ACS data collected in a segmented manner to obtain ACS data in a k-space, wherein the re-sorting is profred such that:

a corresponding line number of the collected ACS data in the p-ith line in any segment p in k-space after re-sorting is R*(pi−1)+p, and wherein 1≤p≤R and pi≥1.

12. The EPI scanning device according to claim 10, wherein the first data collection circuitry is further configured to cause the EPI scanning device to, after the RF excited pulse is applied and before the first RF convergence pulse is applied to the target tissue:

sequentially apply the first RF convergence pulse to the target tissue for preset times at intervals;

apply the second layer selection gradient pulse to the target tissue in the layer selection encoding direction while the first radio-frequency convergence pulse is applied each time; and after the first RF convergence pulse is applied each time, apply the first readout gradient pulse sequence to the target tissue in the readout direction, and simultaneously (i) forbidding the phase encoding gradients in the phase encoding direction, and (ii) turning off the ADC.

13. An echo planar imaging (EPI) scanning device, comprising:

third data collection circuitry configured to cause the EPI Scanning device to perform a single excited EPI scanning process, by:

simultaneously applying a 90° radio-frequency (RF) excited pulse and a first layer selection gradient pulse to a target tissue in a layer selection encoding direction;

after applying the RF excited pulse, simultaneously applying a first RF convergence pulse and a second layer selection gradient pulse to the target tissue in the layer selection encoding direction; and after applying the first RF convergence pulse, simultaneously (i) applying a first readout gradient pulse sequence to the target tissue in a readout direction, and (ii) turning on an analog-digital converter (ADC) to collect data for correcting a phase error between k-space lines while forbidding phase encoding gradients in a phase encoding direction; and fourth data collection circuitry configured to cause the EPI scanning device to:

after applying the first readout gradient pulse sequence, turn off the ADC, sequentially apply the first RF convergence pulse to the target tissue for 2R times at intervals, and apply the second layer selection gradient pulse to the target tissue in the layer selection encoding direction while the first radio-frequency convergence pulse is applied each time;

after applying the first RF convergence pulse each time, applying the first or second readout gradient pulse sequence to the target tissue in the readout direction, simultaneously (i) apply a first phase encoding pulse sequence in the phase encoding direction, and (ii) turn on the analog-digital converter to collect auto calibration signal (ACS) data in a segmented manner, wherein R represents an in-layer phase direction acceleration factor, wherein the first readout gradient pulse sequence is applied to the target tissue at odd-numbered times in the 2R times, wherein the second readout gradient pulse sequence is applied to the target tissue at even-numbered times in the 2R times, each of the first and second readout gradient pulse sequence being formed by a plurality of pairs of gradient pulses with opposite polarities, and the polarity of the first readout gradient pulse sequence being opposite to that of the second readout gradient pulse sequence; and when the first or second readout gradient pulse sequence applied to the target tissue in the readout direction is when the polarity of the gradient pulse changes, apply a phase encoding pulse to the target tissue in the phase encoding direction.

14. The EPI scanning device according to claim 13, wherein the fourth data collection circuitry is further configured to cause the EPI scanning device to:

after simultaneously turning on the analog-digital converter to collect ACS data in a segmented manner, re-sort the ACS data collected in a segmented manner to obtain ACS data in a positive readout gradient k-space and ACS data in a negative readout gradient k-space, wherein the re-sorting is performed such that:

a corresponding line number of the ACS data collected by the l-ith positive readout gradient pulse in any odd-numbered segment l in the positive readout gradient k-space is 2R*(li−1)+ (l+1)/2, a corresponding line number of the ACS data collected by the l-jth negative readout gradient pulse in any odd-numbered segment l in the negative readout gradient k-space is 2R*lj−R+(l+1)/2, a corresponding line number of the ACS data collected by the r-jth negative readout gradient pulse in any even-numbered segment r in the negative readout gradient k-space is 2R*(rj−1)+r/2, and a corresponding line number of the ACS data collected by the r-ith positive readout gradient pulse in any even-numbered segment r in the positive readout gradient k-space is 2R*ri−R+r/2, wherein l≤l≤2R−1, 2≤r≤2R, li≥1, lj≥1, rj≥1, and ri≥1.

15. The EPI scanning device according to claim 13, wherein the third data collection circuitry is further configured to cause the EPI scanning device to:

after the RF excited pulse is applied and before the first RF convergence pulse is applied to the target tissue:

sequentially apply the first RF convergence pulse to the target tissue for preset times at intervals;

apply the second layer selection gradient pulse to the target tissue in the layer selection encoding direction while the first radio-frequency convergence pulse is applied each time; and after the first radio-frequency convergence pulse is applied each time, apply the first readout gradient pulse sequence to the target tissue in the readout direction, and simultaneously (i) forbid the phase encoding gradients in the phase encoding direction, and (ii) turn off the ADC.

16. An echo planar imaging (EPI) scanning device, comprising:

fifth data collection circuitry configured to cause the EPI scanning device to perform a single excited EPI scanning process by:

simultaneously applying a 90° radio-frequency (RF) excited pulse to a target tissue and a first layer selection gradient pulse to a target tissue in a layer selection encoding direction;

after applying the RF excited pulse, simultaneously applying a RF convergence pulse and a second layer selection gradient pulse to the target tissue in the layer selection encoding direction; and after applying the first RF convergence pulse, simultaneously applying a first readout gradient pulse sequence to the target tissue in a readout direction and turning on an analog-digital converter (ADC) to collect data for correcting a phase error between k-space lines while forbidding phase encoding gradients in a phase encoding direction; and sixth data collection circuitry configured to cause the EPI scanning device to:

after applying the first readout gradient pulse sequence, turning off the ADC, sequentially applying the first RF convergence pulse to the target tissue for 2R times at intervals, and applying the second layer selection gradient pulse to the target tissue in the layer selection encoding direction while the first radio-frequency convergence pulse is applied each time;

after applying the first RF convergence pulse each time, simultaneously applying (i) the first readout gradient pulse sequence to the target tissue in the readout direction, (ii) applying a phase encoding pulse sequence in the phase encoding direction, and (iii) turning on the analog-digital converter to collect auto calibration signal (ACS) data in a segmented manner, wherein R represents an in-layer phase direction acceleration factor, and the first readout gradient pulse sequence is formed by a plurality of pairs of gradient pulses with opposite polarities; and when the first readout gradient pulse sequence applied to the target tissue in the readout direction is when adjacent pairs of gradient pulses are alternate, applying a phase encoding pulse to the target tissue in the phase encoding direction.

17. The EPI scanning device according to claim 16, wherein the sixth data collection circuitry is further configured to cause the EPI scanning device to:

after simultaneously turning on the ADC to collect ACS data in a segmented manner:

re-sort the ACS data collected in a segmented manner to obtain ACS data in the k-space, wherein the re-sorting is performed such that:

a corresponding line number of the ACS data collected by the t-ith positive readout gradient pulse in any segment t in a positive readout gradient k-space is $2R^*(ti-1)+t$, and a corresponding line number of the ACS data collected by the t-jth negative readout gradient pulse in any segment 1 in a negative readout gradient k-space is $2R^*(tj-1)+t$, wherein $l \le t \le 2R$, $ti \ge 1$, and $tj \ge 1$.

18. The device according to claim 16, wherein the fifth data collection circuitry is further configured to cause the EPI scanning device to:

after the RF excited pulse is applied and before the first radio-frequency convergence pulse is applied to the target tissue:

sequentially apply the first RF convergence pulse to the target tissue for preset times at intervals;

apply the second layer selection gradient pulse to the target tissue in the layer selection encoding direction while the first radio-frequency convergence pulse is applied each time; and after the first RF convergence pulse is applied each time, apply the first readout gradient pulse sequence to the target tissue in the readout direction, and simultaneously (i) forbid the phase encoding gradients in the phase encoding direction, and (ii) turn off the ADC.

* * * * *